US009163079B2

(12) United States Patent
Poppe

(10) Patent No.: US 9,163,079 B2
(45) Date of Patent: Oct. 20, 2015

(54) MONOSPECIFIC POLYPEPTIDE REAGENTS

(75) Inventor: Robert Poppe, Mainz (DE)

(73) Assignee: Orgentec Diagnostika GmbH, Mainz (DE)

( * ) Notice: Subject to any disclaimer, the term of this patent is extended or adjusted under 35 U.S.C. 154(b) by 0 days.

(21) Appl. No.: 13/512,206

(22) PCT Filed: Nov. 24, 2010

(86) PCT No.: PCT/EP2010/068134
§ 371 (c)(1),
(2), (4) Date: May 25, 2012

(87) PCT Pub. No.: WO2011/064257
PCT Pub. Date: Jun. 3, 2011

(65) Prior Publication Data
US 2012/0276099 A1 Nov. 1, 2012

(30) Foreign Application Priority Data
Nov. 27, 2009 (DE) .......................... 10 2009 047 243

(51) Int. Cl.
*C07K 19/00* (2006.01)
*A61K 39/395* (2006.01)
*C07K 16/18* (2006.01)
*C07K 16/00* (2006.01)

(52) U.S. Cl.
CPC .................. *C07K 16/18* (2013.01); *C07K 16/00* (2013.01); *C07K 2317/35* (2013.01); *C07K 2317/41* (2013.01); *C07K 2317/522* (2013.01); *C07K 2317/524* (2013.01); *C07K 2317/526* (2013.01); *C07K 2317/528* (2013.01); *C07K 2317/622* (2013.01); *C07K 2317/64* (2013.01)

(58) Field of Classification Search
CPC .................. A61K 2039/505; C07K 2317/622; C07K 2317/56
See application file for complete search history.

(56) References Cited

U.S. PATENT DOCUMENTS

2008/0044414 A1* 2/2008 Masat et al. ................ 424/136.1
2009/0053225 A1* 2/2009 Marzari et al. ............. 424/136.1

FOREIGN PATENT DOCUMENTS

| EP | 1757622 A1 | 2/2007 |
| WO | 0151644 A2 | 7/2001 |
| WO | 2005017148 A1 | 2/2005 |
| WO | 2006/117782 A2 | 11/2006 |
| WO | 2007062466 A1 | 6/2007 |
| WO | 2007109321 A2 | 9/2007 |
| WO | 2008012543 A1 | 1/2008 |
| WO | 2008131252 A1 | 10/2008 |
| WO | WO 2008145137 A2 * | 12/2008 |
| WO | 2009135627 A1 | 11/2009 |

OTHER PUBLICATIONS

Carter (Nature Review, 2006, 6:343-357).*
Padlan et al (FASEB Journal, 1995, 9:133-139).*
Burgess et al (Journal of Cell Biology, 1990, 111:2129-2138).*
Lazar et al (Molecular and Cellular Biology, 1998, 8:1247-1252).*
Muraoka et al (Journal of Immunology, 1989, 142:695-701).*
Worn et al (FEBS Letters, 1998, 427:357-361).*
Hu et al (Cancer Research, 1996, 56:3055).*
McAuley et al (Protein Science, 2008, 17:95-106).*
Hust Michael et al: "Single chain Fab (scFab) fragment", BMC Biotechnology, Biomed Central Ltd. London, GB, vol. 7, No. 1, Mar. 8, 2007, p. 14, XP021023594, ISSN: 1472-6750, DOI: DOI:10.1186/1472-6750-7-14 figure 1A.
Le Gall F et al: "Immunosuppressive properties of anti-CD3 single-chain Fv and diabody", Journal of Immunological Methods, Elsevier Science Publishers B.V.,Amsterdam, NL, vol. 285, No. 1, Feb. 1, 2004, pp. 111-127, XP004489671, ISSN: 0022-1759, DOI: D01:10.1016/J.JIM.2003.11.007 p. 113.
Muller K M et al: "The first constant domain (CH1 and CL) of an antibody used as heterodimerization domain for bispecific miniantibodies", FEBS Letters, Elsevier, Amsterdam, NL, vol. 422, No. 2, Jan. 30, 1998, pp. 259-264, XP004261818, ISSN: 0014-5793, DOI: DOI:10.1016/S0014-5793(98)00021-0 figures 1A,1B.
Shao Changli et al: "The expression and characterization of a bifunctional protein in E. coli for autologous erythrocyte agglutination test.", Cellular & Molecular Immunology Aug. 2008 LNKD-PUBMED:18761818, vol. 5, No. 4, Aug. 2008, pp. 299-306, XP002627304, ISSN: 1672-7681 figure 2.
Long M C et al: "Construction and characterization of monoclonal antibodies against western equine encephalitis virus.", Hybridoma Apr. 2000 LNKD-PUBMED:10868791, vol. 19, No. 2, Apr. 2000, pp. 121-127, XP002627305, ISSN: 0272-457X figures 1,2.
Tincani A et al: Minimal requirements for antiphospholipid antibodies ELISAs proposed by the European Forum on antiphospholipid antibodies, Thrombosis Research, Tarrytown, NY, US, vol. 114, No. 5-6, Jan. 1, 2004, pp. 553-558, XP004613201, ISSN: 0049-3848, DOI: DOI:10.1016/J.THROMRES.2004.06.035 the whole document.
Dubel et al.: "Rekombinante Antikorper—Werkzeuge gegen Krebs, Infektionen and Autoimmunerkrankungen ?", Biologie in Unserer Zeit, vol. 34, No. 6, Dec. 2004, pp. 372-379, XP002640338, Weinheim cited in the application figure 4.
Nieba L et al: "Disrupting the hydrophobic patches at the antibody variable/constant domain interface: Improved in vivo folding and physical characterization of an engineered scEv fragment",. Protein Engineering, Oxford University Press, Surrey, GB, vol. 10, No. 4, Jan. 1, 1997, pp. 435-444, XP002249462, ISSN: 0269-2139, DOI: D01:10.1093/Protein/10.4.435 p. 436, left-hand column, last paragraph.

(Continued)

*Primary Examiner* — Misook Yu
*Assistant Examiner* — Julie Wu
(74) *Attorney, Agent, or Firm* — Rothwell, Figg, Ernst & Manbeck, P.C.

(57) ABSTRACT

The present invention relates to a novel antigen-binding protein construct or "modubody", which contains at least three functional single domain modules of an antibody. The modubodies contain a domain from the heavy chain variable region of an antibody (VH), a domain from the light chain variable region of an antibody (VL) and bind monospecifically to an antigen. The modubodies further contain a domain from the constant region of antibodies. The modubodies can be used for diagnostic or therapeutic purposes.

19 Claims, 16 Drawing Sheets

(56) References Cited

OTHER PUBLICATIONS

Olafsen Tove et al: "Characterization of engineered anti-p185HER-2 (scFv-CH3)2 antibody fragments (minibodies) for tumor targeting", Protein Engineering, Design and Selection, Oxford Journal, London, GB, vol. 17, No. 4, Apr. 1, 2004, pp. 315-323, XP002484237, ISSN: 1741-0126, DOI: D0I:10.1093/PROTEIN/GZH040 figures 2a,2b.

Ichikawa K et al: "A chimeric antibody with the human gammal constant region as a putative standard for assays to detect IgG beta2-glycoprotein I-dependent anticardiolipin and anti-beta2-glycoprotein I antibodies.", Arthritis and Rheumatism Nov. 1999 LNKD-PUBMED:10555042, vol. 42, No. 11, Nov. 1999, pp. 2461-2470, XP002640339, ISSN: 0004-3591 the whole document.

Sazinsky Stephen L et al: "Aglycosylated immunoglobulin G1 variants productively engage activating Fc receptors", Proceedings of the National Academy of Sciences, National Academy of Sciences, vol. 105, No. 51, Dec. 23, 2008, pp. 20167-20172, XP009143223, ISSN: 0027-8424, DOI: D01:10.1073/PNAS.0809257105 figures 1,2c.

Wu A M et al: "Multimerization of a chimeric anti-CD20 single-chain Fv-Fc fusion protein is mediated through variable domain exchange", Protein Engineering, Oxford University Press, Surrey, GB, vol. 14, No. 12, Jan. 1, 2001, pp. 1025-1033, XP002982160, ISSN: 026 9-2139, DOI: DOI;10.1093/PROTEIN/14.12.1025 p. 1025, left-hand col. p. 1028, left-hand column.

Li Erqiu et al: "Mammalian cell expression of dimeric small immune proteins (SIP)", Protein Engineering, Oxford University Press, Surrey, GB, vol. 10, No. 6, Jan. 1, 1997, pp. 731-736, XP002252049, ISSN: 0269-2139, DOI: DOI:10.1093/PROTEIN/10.6.731 figure 1.

A. Schouten: "Plantibodies : requirements for expression and subcellular targeting", 1998, XP002640340, Retrieved from the Internet: URL:http://library.wur.nl/WebQuery/wda/lan g?dissertatie/nummer=2513 [retrieved on Jun. 7, 2011] abstract.

Trinh et al., "Optimization of codon pair use within the (GGGGS)3 linker sequence results in enhanced protein expression", Molecular Immunology, 40(2004), pp. 717-722.

Gargano et al., "Rescue of a neutralizing anti-viral antibody fragment from an intracellular polyclonal repertoire expressed in mammalian cells", FEBS Letters, 414 (1997), pp. 537-540.

Jung et al., "Improving in vivo folding and stability of a single-chain Fv antibody fragment by loop grafting", Protein Engineering , vol. 10, No. 8, 1997, pp. 959-966.

Dimitrov et al., Engineered CH2 domains (nanoantibodies); Landes Bioscience, vol. 1, Issue 1, Jan./Feb. 2009, pp. 26-28.

* cited by examiner

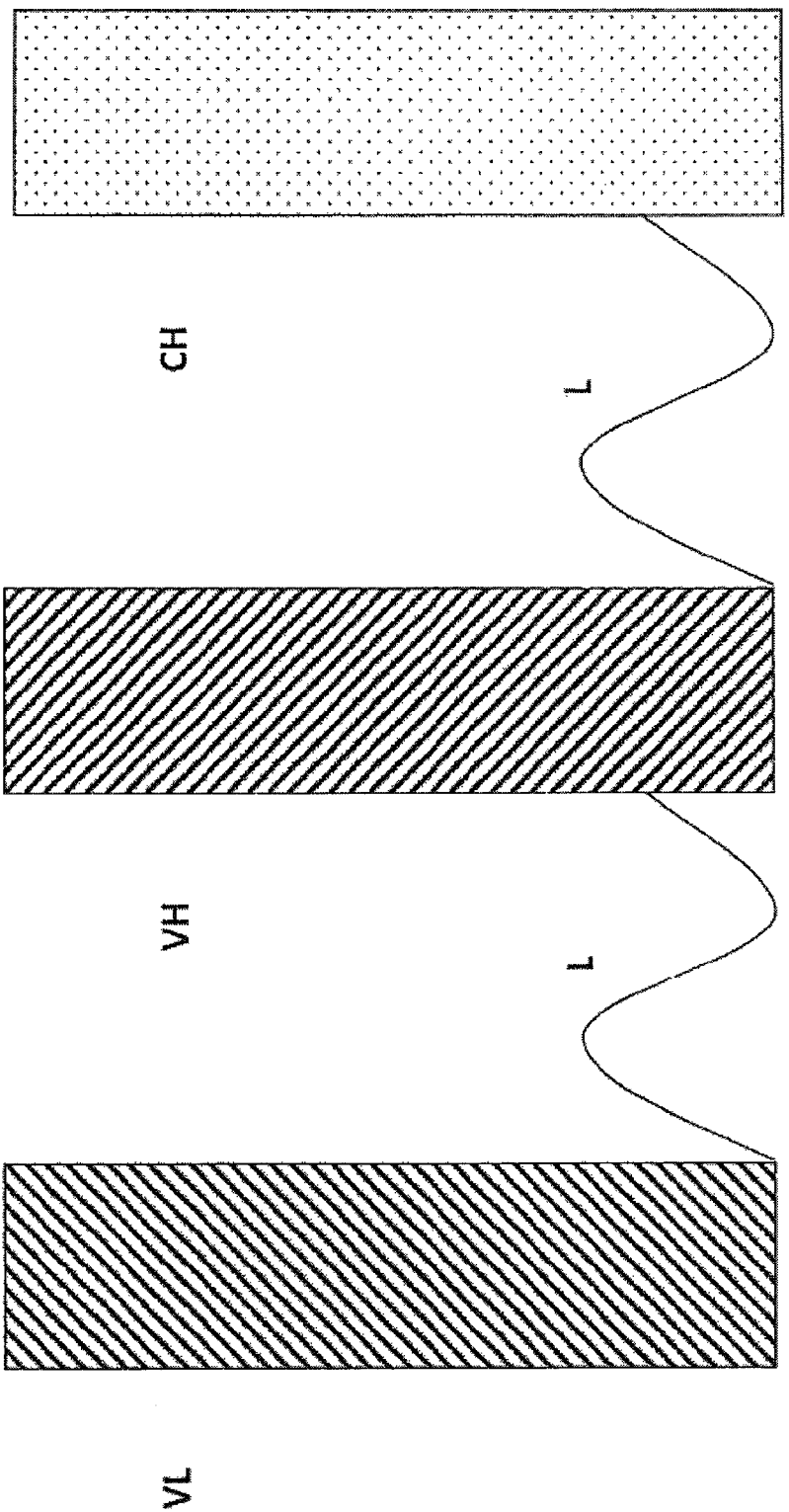

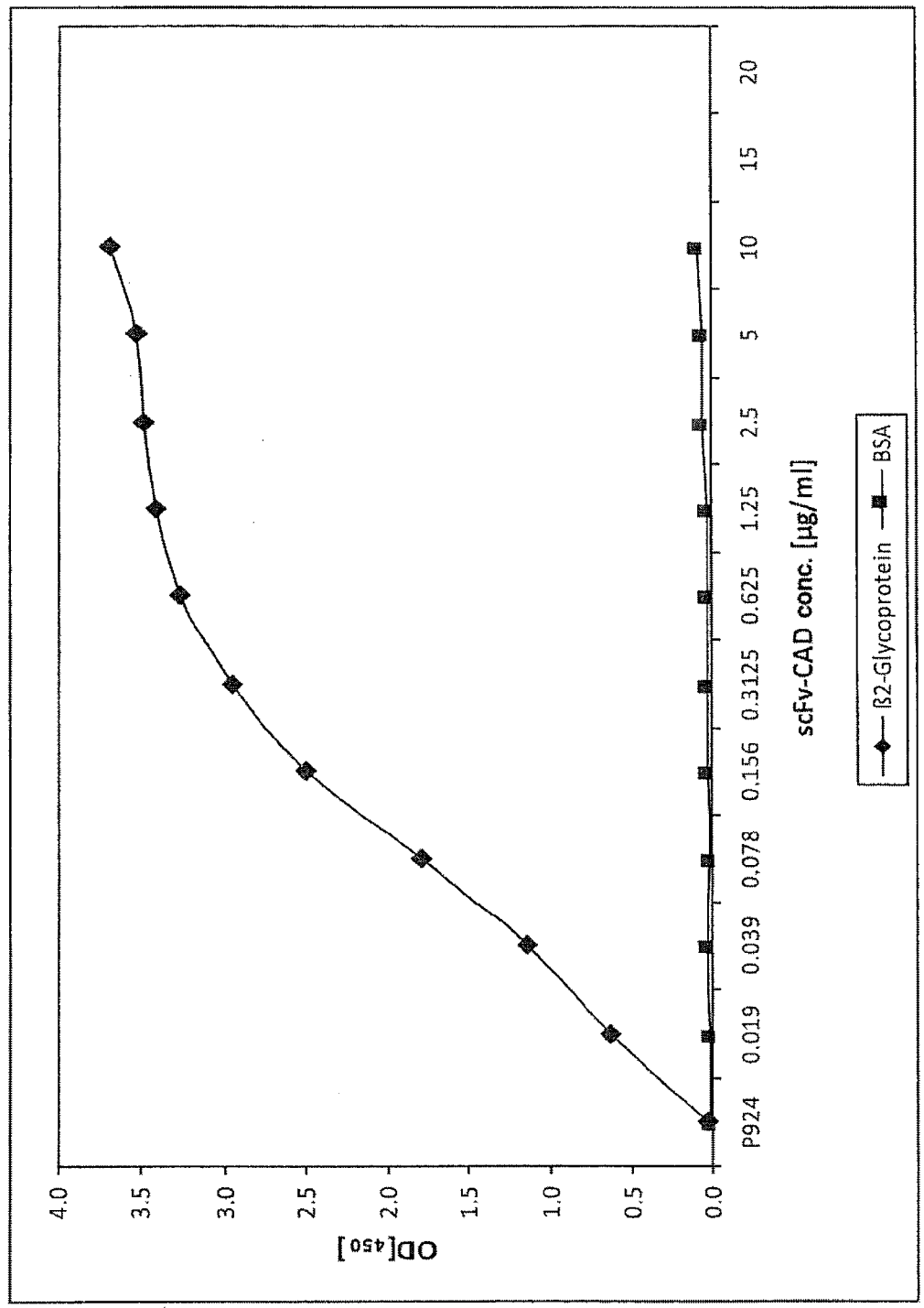

MONOSPECIFIC POLYPEPTIDE REAGENTS

CROSS REFERENCE TO RELATED APPLICATION

This application is a 35 U.S.C. 371 National Phase Entry Application from PCT/EP2010/068134, filed Nov. 24, 2010, which claims the benefit of German Patent Application No. 10 2009 047 243.6 filed on Nov. 27, 2009, the disclosures of which are incorporated herein in their entirety by reference.

DESCRIPTION

The present invention relates to a novel antigen-binding protein construct or "modubody", which contains at least three functional single domain modules of an antibody. The modubodies contain a domain from the heavy chain variable region of an antibody (VH), a domain from the light chain variable region of an antibody (VL) and bind monospecifically to an antigen. The modubodies further contain a domain from the constant region of antibodies. The modubodies can be used for diagnostic or therapeutic purposes.

BACKGROUND OF THE INVENTION

Antibody Structure

Antibodies are plasma glycoproteins, which consist of a plurality of polypeptide chains connected by disulphide bridges. A standard antibody consists of two identical heavy immunoglobulin (Ig) chains and two identical light chains. Both antibody chains consist of different protein domains having a length of about 110 amino acid residues, which are composed of β-sheets in the form of a characteristic immunoglobulin fold. The heavy chain consists of one variable (VH) domain and three or four constant domains (CH1, CH2, CH3, CH4). The light chain consists of one variable (VL) and one constant (CL) domain. The variable portions of the heavy and light chain, in particular the hypervariable complementarity determining regions (CDR), contribute to antigen specificity. The immune system provides a high diversity of antibodies against very different antigens. Antibodies can be assigned to different classes, for example IgM, IgA, IgG, IgE, IgD.

Antibody Fragments and Substructures

Antibody fragments can be obtained by enzymatic cleavage or by recombinant processes. A Fab fragment equipped with the antigen recognition function contains the VH-CH1 domains of the heavy chain and the VL-CL domains of the light chain, connected together via disulphide bridges, while the Fv fragment comprises only the heavy and light chain variable regions. However, these fragments consisting of a plurality of protein subunits can be prepared in biologically active form in an acceptable yield only by complex processes (Read et al. (2007), Appl. Environ. Microbiol. 73: 5088-5096).

A single-chain Fv fragment (scFv) is a small, approximately 28 kDa heavy antigen-binding substructure in the form of a covalent coupling of VH and VL domains via a peptide linker (Hu et al. (1996), Cancer Res 56: 3055-3061). However, the folding efficiency, the sometimes inadequate stability and the toxicity of these structures frequently limit the yield in the preparation of biologically active scFv in bacterial expression systems (Nieba et al. (1997), Protein Eng 10: 435-444).

The term minibody (mini-antibody) refers to an approximately 75 kDa heavy chimeric molecule of an scFv and a hinge region from the heavy chain fused with the CH3 domain which, assisted by the CH3 domain, is assembled to form a bivalent molecule covalently bonded via disulphide bridges of the hinge region (Wu, EP0627932B1). The CH3 domain serves as the dimerisation domain for the production of homodimers (cf. Dübel et al., Biol. Unserer Zeit, Vol. 34, No. 6, p. 372-379, 2004). However, on expression in E. coli, these molecules exhibit low expression rates and proteolytic degradation in the hinge region (Hu et al. (1996), Cancer Research 56: 3055-3061).

Like the minibody, the diabody has two antigen-binding sites. In the diabody, VL and VH domains are connected in the form of a single polypeptide chain to give a divalent and bispecific molecule (Hollinger et al. (1993), PNAS 90: 6444-6448).

Monobodies are chimeric antigen-binding polypeptides, which exhibit hypervariable CDR loops within a fibronectin type III scaffold (Koide, EP0985039B1). These molecules provide a valuable class of novel affinity reagents. However, when CDR loops are transplanted into a heterologous fibronectin scaffold, effector and detection functions of native antibodies are lost.

Nanobodies consist of single-chain antigen-binding $V_H H$ domains (variable domains of a heavy chain antibody) and are based on the observation that natural and functional antibodies that consist only of heavy chains are found in camels and llamas (Caserman and Harmers, EP 19930919098). The solubility of human VH domains (heavy chain variable domains) is, however, frequently limited on account of hydrophobic regions, which interact in the intact antibody with regions of the light chain (Barthelemy et al. (2007) J. Biol. Chem. 283: 3639-3654).

Antibodies in Immunodiagnosis

There are numerous immunoassay formats for determining the presence or concentration of a specific antibody, for example against a pathogen, an autoantigen or an allergen, in a biological sample. In general, such assays are directed to the detection of a specific antibody class or a combination of particular antibody classes and use specific internal controls or calibrators. Immunoassays which are suitable, for example, for determining human autoantibodies generally contain a positive control, a negative control and an index calibrator or a gradation of different calibrator concentrations (standard series) for producing a calibration curve, with which antibody concentrations in a sample can be interpolated. Such control and calibration reagents are conventionally prepared by diluting seropositive plasmas or serums in a suitable dilution medium.

For example, the calibrators and controls for the isotype-specific determination of β2-glycoprotein autoantibodies are prepared from the serum of human donors, which contain high concentrations of these autoantibodies of classes IgG, IgM and/or IgA. The use of human seropositive serum or plasma to prepare controls and calibrators is associated with numerous disadvantages, however, such as, for example, the difficulty of acquiring such reagents in large amounts and of suitable quality, differences in the binding characteristics in different batches, heterogeneous polyclonal specificity, heterogeneous isotype composition, presence of pathogens, costs, etc.

Because antibodies bind to antigens with high specificity and affinity, they are of central importance in immunodiagnosis. The size of the natural molecules and their complex structure of a plurality of polypeptide chains with a large number of inter- and intra-domains, interconnections through disulphide bridges as well as glycosylation positions represent a considerable obstacle in the construction and the recombinant expression of specific antibodies.

Hackett et al. (EP1018019 B1) disclose a process for the preparation of reagents for use as calibrators and controls, wherein the reagent is a chimeric monoclonal antibody which comprises heavy and light chain variable regions from a first host species fused to heavy and light chain constant regions from a second host species, which corresponds to that of the antibody to be determined. However, the preparation of these species-chimeric monoclonal antibodies requires a high technical outlay, as is typical of the production of monoclonal antibodies. Although Hackett mentions the theoretical possibility of using as synthetic calibrators also polypeptides which bind specifically to a given ligand and are fused to an antibody region of the desired host species, Hackett does not provide a process by means of which single-chain synthetic polypeptide calibrators can be synthesised.

There is accordingly a continuing need for small, antibody-like molecules which specifically recognise an antigen, form complexes with antibodies against natural immunoglobulins, and can be prepared easily and in a large amount in bacterial expression systems.

SUMMARY OF THE INVENTION

The invention provides a monovalent fusion polypeptide comprising
(i) a first domain comprising the heavy chain variable region of an antibody (VH) or at least a section thereof that mediates antigen binding,
(ii) a second domain comprising the light chain variable region of an antibody (VL) or at least a section thereof that mediates antigen binding, and
(iii) a third domain comprising a section of a heavy chain constant region of an antibody (CHX),
wherein domains (i), (ii) and (iii) are linked together via peptide linkers (L).

The invention further provides a nucleic acid which codes for a monovalent fusion polypeptide as described above.

The invention still further provides a host cell which contains a nucleic acid according to the invention.

The invention still further provides a process for the preparation of a monovalent fusion polypeptide by cultivating a host cell according to the invention and obtaining the fusion polypeptide from the cell or from the culture supernatant.

Yet further aspects of the present invention relate to the use of monovalent fusion polypeptides as reagents in diagnostic or biochemical tests, as well as to medical applications of the fusion polypeptides, nucleic acids and host cells.

The monovalent fusion polypeptides according to the invention are referred to as "modubodies".

Modubodies are constructs which consist of domains of the variable heavy (VH) and variable light (VL) chains of an antibody and one or more domains of the heavy chain constant region (CH1, CH2, CH3, CH4) of antibodies, these domains of an antibody being coupled together in the form of a linear sequence of independently structured function modules via suitable linker sequences. The individual domains have a length of, for example, from 80 to 130 amino acids. Modubodies consist of a single polypeptide chain and possess a single antigen-binding site, which is formed of the domains VH and VL. Modubodies are preferably unable to form intermolecular disulphide bridges, so that they are present in the form of monomers. Modubodies are free of hinge regions of antibodies. They are accordingly miniature versions of monovalent antibodies, which can be prepared simply and in large amounts in the form of a single protein chain in suitable expression systems, for example bacterial expression systems. Owing to their single-chain structure, their small size, the monoclonal composition, the fact that they can be prepared easily, and their stability, modubodies are ideal reagents for biochemical research, for use in diagnostic assays and as therapeutic agents.

Accordingly, a modubody is a chimeric molecule having a typical structure as in FIG. 1, consisting of separate function modules which are derived from domains of the variable heavy (VH) and variable light (VL) chains of an antibody and one or more domains of the heavy chain constant region (CHX, e.g. CH1, CH2, CH3 or CH4) of antibodies. The individual independently structured function modules are coupled together in a linear sequence via suitable linker sequences (L).

DESCRIPTION OF THE FIGURES

FIG. 1:
Schematic structure of an embodiment of a fusion polypeptide (modubody) according to the invention, wherein VL denotes a domain of the variable light chain, VH denotes a domain of the variable heavy chain, and CHX denotes a domain of the heavy chain constant region (CH1, CH2, CH3 or CH4) of antibodies. The individual domains are connected together in a linear sequence by heterologous, preferably flexible peptide linkers L.

FIG. 2:
Characterisation of the binding reaction of an scFV-CAD reaction module to the target β2-glycoprotein.

For the ELISA detection of the specific β2-glycoprotein-binding activity of the scFv-CAD reaction module, serial dilutions of scFv-CAD in the indicated concentration were applied to microtitre plates coated with β2-glycoprotein and, for control purposes, with bovine serum albumin (BSA). The binding was determined using a peroxidase-labelled RGS-6X-His antibody (Qiagen, Hilden) and a tetramethylbenzidine (TMB) colour reaction by measurement of the O.D. 450.

FIG. 3:
Characterisation of the stability of an scFV-CAD reaction module to temperature stress.
A. In order to investigate the influence of 50° C. temperature stress on the β2-glycoprotein-binding activity of the CAD-scFv, the purified protein module in a concentration of 5 μg/ml was exposed to a temperature of 50° C. for a period of 0-180 minutes. The binding of the scFv-CAD to β2-glycoprotein was determined in an ELISA using a peroxidase-labelled RGS-6X-His antibody and a TMB colour reaction by measurement of the O.D. 450.
B. In order to determine the inactivation temperature of the scFv-CAD, the purified protein module in a concentration of 5 μg/ml in calibrator dilution medium was exposed to a series of temperatures of from 20° C. to 90° C. for 10 minutes. The binding of the scFv-CAD to β2-glycoprotein was determined in an ELISA using a peroxidase-labelled RGS-6X-His antibody and a TMB colour reaction by measurement of the O.D. 450.

Figure 4:
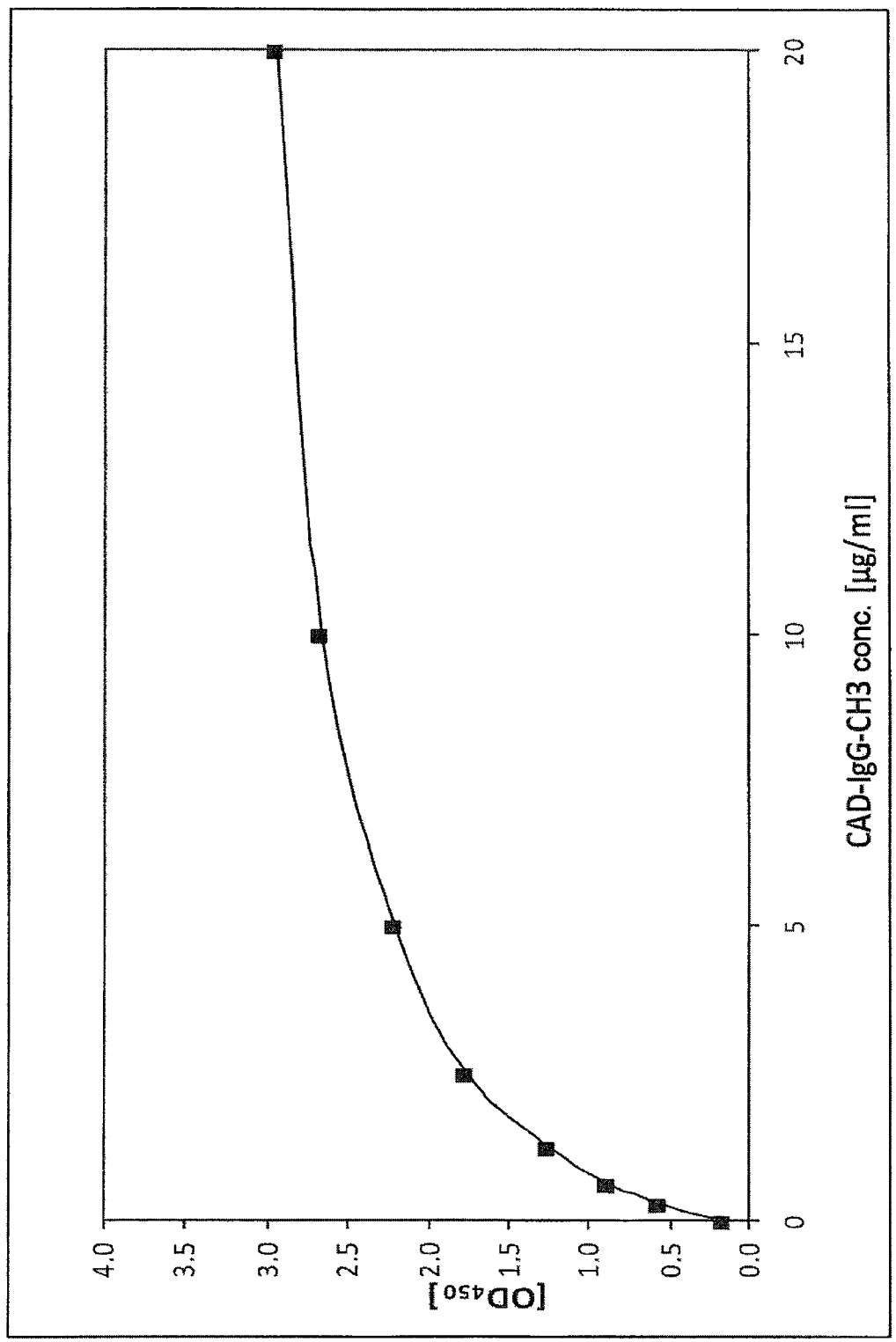

FIG. 4:
Characterisation of the calibrator function of a CAD-IgG-CH3 modubody by binding to the target β2-glycoprotein and detection with an antihuman IgG peroxidase secondary antibody. CAD-IgG-CH3 was applied in the indicated concentration to microtitre plates coated with β2-glycoprotein, and the binding was determined using a peroxidase-labelled anti-human IgG antibody (Jackson Immunoresearch) and a TMB colour reaction by measurement of the O.D. 450.

Figure 5:
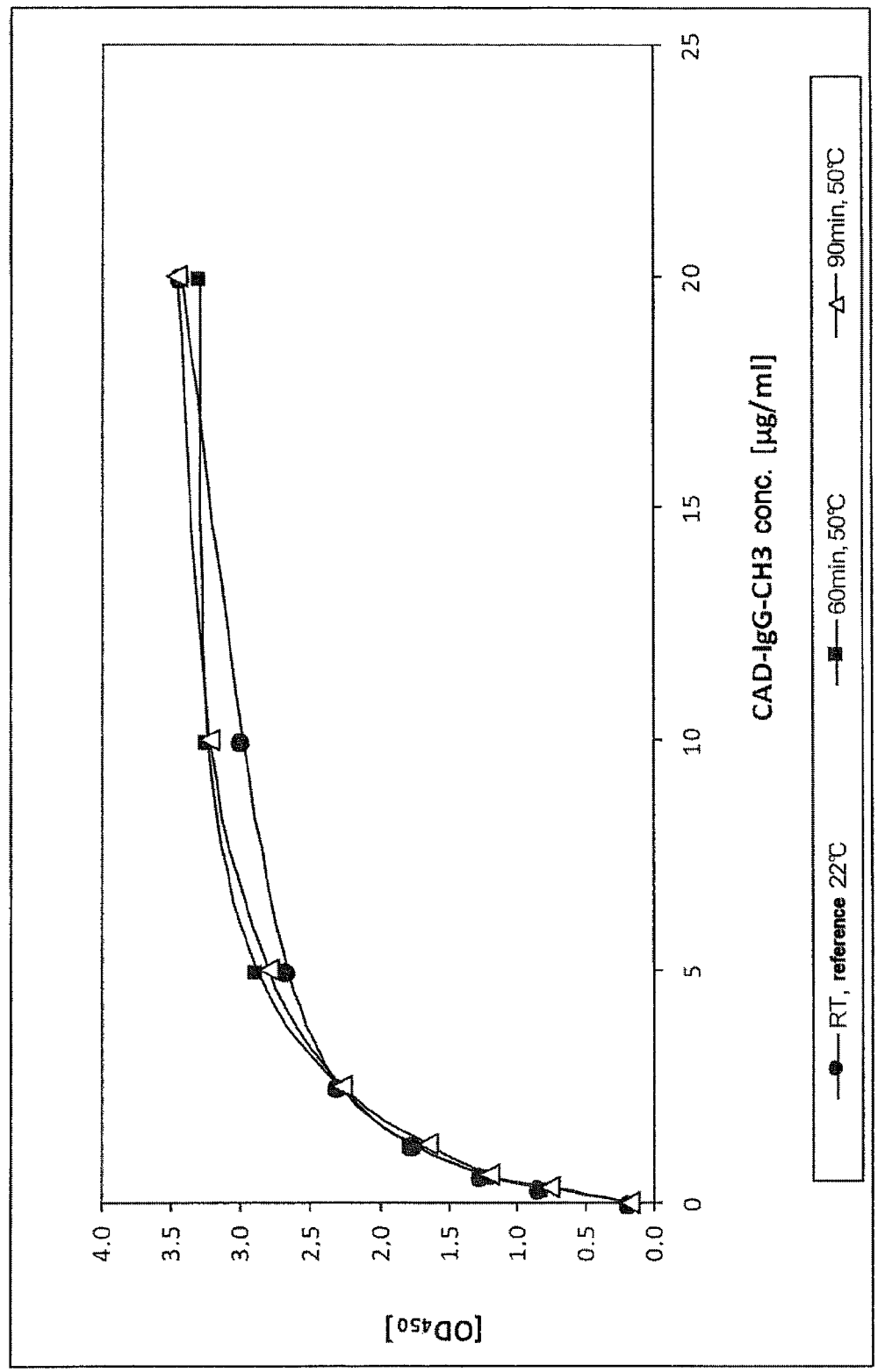

FIG. 5:
Characterisation of the stability of a CAD-IgG-CH3 modubody to temperature stress. The stability to heat stress was investigated as follows: dilutions of the CAD-IgG-CH3 modubody in the indicated concentrations were incubated for 60 minutes and 90 minutes at 50° C. and investigated in an anti-β2-glycoprotein immunoassay in comparison with a dilution series stored at room temperature. The binding of the CAD-IgG-CH3 modubody to β2-glycoprotein was determined using a peroxidase-labelled antihuman IgG antibody and a TMB colour reaction by measurement of the O.D. 450.

FIG. 6:

Characterisation of the stability of a CAD-IgG-CH3 modubody to storage at 36° C. The stability to elevated storage temperature was investigated as follows: dilutions of the CAD-IgG-CH3 modubody in the indicated concentrations were incubated for 1, 2, 4, 7, 10 days at 36° C. and investigated in an anti-β2-glycoprotein immunoassay in comparison with a dilution series stored at 4° C. The binding of the CAD-IgG-CH3 modubody to β2-glycoprotein was determined using a peroxidase-labelled antihuman IgG antibody and a TMB colour reaction by measurement of the O.D. 450.

FIG. 7:

Characterisation of the stability of a CAD-IgG-CH3 modubody to drying. The stability to drying was investigated as follows: dilutions of the CAD-IgG-CH3 modubody were dried in vacuo at 22° C. in a Speedvak device and then resolubilised to the indicated concentrations. The binding of the resolubilised CAD-IgG-CH3 modubody to β2-glycoprotein was then determined using a peroxidase-labelled antihuman IgG antibody and a TMB colour reaction by measurement of the O.D. 450.

FIG. 8:

Characterisation of the stability of a CAD-IgG-CH3 modubody to repeated freeze-thaw cycles. The stability to repeated freeze-thaw cycles was investigated as follows: dilutions of the CAD-IgG-CH3 modubody were frozen at −70° C. and thawed again at 37° C. in five repeated freeze-thaw cycles and then investigated in the indicated concentrations in an anti-β2-glycoprotein immunoassay. The binding of the CAD-IgG-CH3 modubody to (β2-glycoprotein was determined using a peroxidase-labelled antihuman IgG antibody and a TMB colour reaction by measurement of the O.D. 450.

FIG. 9:

Characterisation of the calibrator function of the CAD-IgG-CH2 modubody by binding to the target β2-glycoprotein and detection with an antihuman IgG peroxidase secondary antibody. CAD-IgG-CH2 was applied in the indicated concentration to microtitre plates coated with β2-glycoprotein in complex with cardiolipin, and the binding was determined using a peroxidase-labelled antihuman IgG antibody (Jackson Immunoresearch) and a TMB colour reaction by measurement of the O.D. 450 nm.

FIG. 10:

Characterisation of the stability of the CAD-IgG-CH2 modubody to drying. The stability to drying was investigated as follows: dilutions of the CAD-IgG-CH2 modubody were dried in vacuo at 22° C. in a Speedvak device and then resolubilised to the indicated concentrations. The binding of the resolubilised CAD-IgG-CH2 modubody to β2-glycoprotein was then determined using a peroxidase-labelled antihuman IgG antibody and a TMB colour reaction by measurement of the O.D. 450 nm.

FIG. 11:

Characterisation of the stability of the CAD-IgG-CH2 modubody to repeated freeze-thaw cycles. The stability to repeated freeze-thaw cycles was investigated as follows: dilutions of the CAD-IgG-CH2 modubody were frozen at −70° C. and thawed again at 37° C. in five repeated freeze-thaw cycles and then investigated in the indicated concentrations on microtitre plates coated with β2-glycoprotein in complex with cardiolipin. The binding of the CAD-IgG-CH2 modubody to β2-glycoprotein was determined using a peroxidase-labelled antihuman IgG antibody and a TMB colour reaction by measurement of the O.D. 450 nm.

FIG. 12:

Characterisation of the calibrator function of the multifunctional CAD-IgM-IgA-IgG modubody by binding to the target β2-glycoprotein and separate detection with the isotype-specific antihuman IgM, antihuman IgA and antihuman IgG peroxidase secondary antibodies. CAD-IgM-IgA-IgG was applied in the indicated concentration to microtitre plates coated with β2-glycoprotein in complex with cardiolipin, and the binding was determined in separate determinations using isotype-specific peroxidase-labelled antihuman IgM, antihuman IgA and antihuman IgG antibodies (Jackson Immunoresearch) and a TMB colour reaction by measurement of the O.D. 450 nm.

FIG. 13:

Characterisation of the stability of the CAD-IgM-IgA-IgG modubody to drying. The stability to drying was investigated as follows: dilutions of the CAD-IgM-IgA-IgG modubody were dried in vacuo at 22° C. in a Speedvak device and then resolubilised to the indicated concentrations. The binding of the resolubilised CAD-IgM-IgA-IgG modubody to β2-glycoprotein was then determined in separate determinations using isotype-specific peroxidase-labelled antihuman IgM, antihuman IgA and antihuman IgG antibodies (Jackson Immunoresearch) and a TMB colour reaction by measurement of the O.D. 450 nm.

FIG. 14:

Characterisation of the stability of the CAD-IgM-IgA-IgG modubody to repeated freeze-thaw cycles. The stability to repeated freeze-thaw cycles was investigated as follows: dilutions of the CAD-IgM-IgA-IgG modubody were frozen at −70° C. and thawed again at 37° C. in five repeated freeze-thaw cycles and then investigated in the indicated concentrations on microtitre plates coated with β2-glycoprotein in complex with cardiolipin. The binding of the CAD-IgM-IgA-IgG modubody to β2-glycoprotein was then determined in separate determinations using isotype-specific peroxidase-labelled antihuman IgM, antihuman IgA and antihuman IgG antibodies (Jackson Immunoresearch) and a TMB colour reaction by measurement of the O.D. 450 nm.

FIG. 15:

Characterisation of the binding reaction of the CAD-IgG-CH3-Knob02 modubody to the target β2-glycoprotein. For the ELISA detection of the specific β2-glycoprotein-binding activity of the CAD-IgG-CH3-Knob02 modubody, serial dilutions of CAD-IgG-CH3-Knob02 in the indicated concentration were applied to microtitre plates coated with β2-glycoprotein and, for control purposes, with bovine serum albumin (BSA). The binding was determined using a peroxidase-labelled RGS-6X-His antibody (Qiagen, Hilden) and a tetramethylbenzidine (TMB) colour reaction by measurement of the O.D. 450 nm.

DETAILED DESCRIPTION OF THE INVENTION

Processes known hitherto for the preparation of antibodies, antibody fragments and small antibody-like molecules have numerous limitations as regards the possibility of preparing them inexpensively in biologically active form.

Processes known hitherto for the production of calibrators and standard materials for diagnostic assays have numerous disadvantages as regards availability, uniform binding and stability characteristics, ensuring the absence of pathogens, and production costs. These limitations and disadvantages are eliminated by the present invention. In addition, there is a continuing need for small antibody-like molecules which specifically recognise an antigen and form complexes with antibodies against natural immunoglobulins.

The present invention permits the preparation of monospecific polypeptide reagents—"modubodies"—for biochemical research, for use in diagnostic assays or as a constituent of therapeutic agents.

A modubody is a chimeric single-chain fusion polypeptide which consists of at least three domains, namely a first domain from the heavy chain variable region of an antibody (VH), a second domain from the light chain variable region of an antibody (VL) and a third domain comprising a part-section of a heavy chain constant region of an antibody (CHX). The individual domains are linked together via suitable peptide linkers. The modubody is monovalent, that is to say it has a single antigen-binding site.

For example, the modubodies according to the invention have a structure (beginning at the N-terminus) as follows:

VH-L-VL-L-CHX or

VL-L-VH-L-CHX, wherein VH denotes the heavy chain variable region of an antibody or at least a section thereof that mediates antigen binding, VL denotes the light chain variable region of an antibody or at least a section thereof that mediates antigen binding, L denotes a peptide linker, and CHX denotes a domain comprising a part-section of a heavy chain constant region of an antibody. CHX can be chosen, for example, from sections CH1, CH2, CH3 and CH4 from the heavy chain constant region of antibodies, preferably of antibodies of classes IgG, IgM, IgE and IgA, particularly preferably of human antibodies of the classes IgG, IgM, IgE and IgA. Preferred examples of the domain CHX are IgG-CH1, IgG-CH2, IgG-CH3, IgA-CH2, IgA-CH3, IgM-CH2, IgM-CH3 and IgM-CH4 or combinations thereof, in particular from the respective human antibodies.

The first domain (VH) and the second domain (VL) together form the antigen-binding site (binding module). They are preferably so chosen that they both originate from a single original antibody. The original antibody is any desired monoclonal antibody, for example a monoclonal antibody from a non-human mammalian species (e.g. rat, mouse or rabbit), a human antibody or a humanised antibody.

The modubody can be directed against any desired antigen, for example a diagnostically or therapeutically relevant antigen. Preferred examples of specific antigens are β2-glycoprotein, phosphatidylserine, vascular endothelial growth factor (VEGF-A), tumour necrosis factor (TNF-alpha), smoothened homolog (SMO), protein patched homolog (PTC1), B-lymphocyte antigen (CD20), cytotoxic T-lymphocyte protein 4 (CTLA4), amyloid beta A4 protein (APP), presenilin-1 (PS1), CC-chemokine receptor (CCR-5), telomere repeat-binding factor 1 (TRF1) and toll-like receptors (TLR1-10).

The first and second domains of the polypeptide according to the invention can contain the complete heavy or light chain variable regions of an antibody or at least a section thereof that mediates antigen binding. Preferably, the domains contain at least the regions CDR1, CDR2 and CDR3 of the heavy or light chain region in question in their entirety and at least parts of the corresponding framework regions FR1, FR2, FR3 and FR4. The length of the domains VH and VL is usually at least 80, at least 90 or at least 100 amino acid residues and up to 110 or up to 120 amino acid residues.

The fusion polypeptide according to the invention contains at least one domain comprising a section of a heavy chain constant region of an antibody (CHX). Preferably, the third domain or the third domains is/are arranged C-terminally to the VH and VL domains. A third domain can contain a complete section from a heavy chain constant region or a part-section thereof which imparts sufficient structural stability to the fusion polypeptide. The length of a third domain is usually at least 80, at least 90 or at least 100 amino acid residues and up to 110, up to 120 or up to 130 amino acid residues. The fusion polypeptide can optionally contain a plurality of third domains which can be identical or different, for example 2, 3 or 4. If a plurality of third domains is present, they are linked together via peptide linkers and are preferably arranged at the C-terminus of the fusion polypeptide. Examples of the structural configuration of fusion polypeptides according to the invention with 2 (or 3) third domains are as follows:

VL-L-VL-L-CHX1-L-CHX2(-L-CHX3) or

VL-L-VH-L-CHX1-L-CHX2(-L-CHX3), wherein VH, L and VL are as defined above and CHX1, CHX2 and CHX3 each denote a third domain CHX as defined above.

The fusion polypeptide according to the invention contains first, second and third domains which are linked together via peptide linkers (L). The peptide linkers consist of sequences which are heterologous to the amino acid sequences of the first, second and third domains, or of sequences which are not present in natural immunoglobulins. The peptide linkers which link the individual domains together can in each case be identical or different. Usually, the peptide linkers each independently have a length of from 10 to 50, preferably from 25 to 45 and particularly preferably from 30 to 40 amino acid residues. It is further preferred for the peptide linkers to be flexible linkers without a secondary structure. For example, suitable peptide linkers consist of at least 80% or at least 90%, preferably at least 95% or completely of glycine and/or serine residues. Particularly suitable are peptide linkers which contain a plurality of sequences SGGGG. A particularly preferred example of a peptide linker is shown in SEQ ID NO: 3. Linker sequences can optionally also be present at the N- and/or C-terminus of the fusion polypeptide.

In addition to domains (i), (ii) and (iii) and the peptide linkers arranged between the domains, the fusion polypeptide can optionally also contain further sequence sections, for example a signal peptide section which is arranged at the N- and/or C-terminus and facilitates the expression and/or secretion of the polypeptide. The fusion polypeptide can further contain one or more additional non-immunoglobulin domains, for example detection or recognition domains, that is to say peptide sequences suitable for the detection or recognition of the fusion polypeptide (tags), for example a FLAG epitope or a poly-His sequence. In addition, the fusion polypeptide can optionally also contain one or more non-immunoglobulin effector domains. The additional domains—where present—are preferably connected to the remainder of the fusion polypeptide via a peptide linker, for example a peptide linker as defined above.

Particularly preferred examples of fusion polypeptides according to the invention contain one or more domains VH, VL and/or CHX as defined above which have at least 90% identity, preferably at least 95% identity, at amino acid level with the corresponding domains according to SEQ ID NO: 1 (VL), SEQ ID NO: 2 (VH), SEQ ID NO: 4 (VH, VL), SEQ ID NO: 8 (IgG-CH1), SEQ ID NO: 10 (IgG-CH2), SEQ ID NO: 12 (IgG-CH3), SEQ ID NO: 14 (IgA-CH2), SEQ ID NO: 16

(IgA-CH3), SEQ ID NO: 18 (IgM-CH2), SEQ ID NO: 20 (IgM-CH3) or SEQ ID NO: 22 (IgM-CH4).

The fusion polypeptide according to the invention can optionally have one or more modifications with respect to the natural sequence of the VH, VL and CHX domains contained therein. For example, at least one asparagine residue at a glycosylation position, for example in a CHX domain, can be replaced by a different amino acid residue, preferably serine, alanine or glycine. Furthermore, at least one cysteine residue, for example in a CHX domain, which does not form a disulphide bridge with a second cysteine residue present in the domain in question and therefore potentially effect the formation of intermolecular disulphide bridges, can optionally be replaced by a different amino acid residue, preferably serine, alanine or glycine.

The modubodies according to the invention are artificial monospecific antibody-like molecules which, in the form of a single protein chain, can easily be prepared in large amounts in suitable expression systems, for example bacterial expression systems. As reagents for biochemical or diagnostic assays, modubodies can specifically bind an antigen via a binding module (VH+VL) and can specifically be detected via a reaction module (CHX) with species- and isotype-specific secondary antibodies. A sequence of a plurality of reaction modules (e.g. CHX1 and CHX2 or CHX and a non-immunoglobulin detection or recognition domain) permits detection with different reagents, for example with different species- or isotype-specific secondary antibodies. As reagents for therapeutic functions, modubodies can bind specifically to an antigen on a target structure via a binding module and exert specific effector functions via a reaction module (CHX) or a series of reaction modules (e.g. CHX1 and CHX2 or CHX and a non-immunoglobulin effector domain). CHX domains which could potentially form dimers are preferably so modified that dimerisation can be ruled out and the modubodies are present in monovalent form.

For example, amino acid positions whose side chains exhibit interactions according to the concept of the "knobs-into-holes" arrangement (Crick, F. H. C. (1952), Nature, 170: 882-883) can be modified.

Accordingly, amino acid positions whose side chains form contacts at the interface of $IgG_1$-CH3 dimers (Ridgway J. B. B. et al. (1996), Protein Engineering, 9: 617-621) can be so modified that bulky amino acid side chains are present at opposing contact sites in the IgG-CH3 dimer and dimerisation is sterically hindered by this "knob-knob" position. The interactions between the contacting amino acid side chains of two $IgG_1$-CH3 domains can be blocked, for example, by replacing the amino acid positions threonine 366, threonine 394, phenylalanine 405 by tyrosine at positions 366, 394 and 405 (numbering scheme according to the Kabat EU Index (Kabat et al., (1991) *Sequences of Proteins of Immunological Interest* 5th Edition, NIH Publication 91-3242)).

The modubodies according to the invention are additionally distinguished by surprising stability, for example stability to temperature stress or stability to drying/reconstitution or freeze/thaw cycles. For example, in comparison with an untreated sample, over 90% of the antigen-binding activity remains, even in dilute solutions (5 µg/ml) of the modubodies, after 10 days' incubation at 36° C. or after drying and reconstitution or after freeze/thaw cycles repeated 5 times.

The de novo construction of a modubody preferably comprises the steps:
a) selection of spatially delimited domains from immunoglobulins of known or modelled spatial structure having regard to sequence and structure data bank information;
b) disulphide bridge optimisation of the selected domains, in which cysteine positions which, in the context of the intact immunoglobulin, form disulphide bridges outside the chosen domains are edited to a structurally neutral amino acid, preferably serine, alanine or glycine;
c) optional editing of asparagine-coupled glycosylation positions preferably to serine, alanine or glycine;
d) linking of a selection of the function modules resulting from steps a) to c) with flexible linker sequences which preferably consist predominantly of the amino acids glycine and/or serine and particularly preferably correspond to the linker sequence (SEQ ID NO: 3), wherein, in dependence on the position of the function module within the modubody and on the cloning strategy, a module sequence resulting from steps a) to c) can be linked with a flexible linker sequence and the linker sequence can form the N- or C-terminus of the function module, and wherein an amino acid sequence which comprises a plurality of function modules or an amino acid sequence forming the complete modubody can optionally be generated;
e) translation of the amino acid sequences resulting from steps a) to d) into corresponding DNA sequences, preferably having regard to a codon frequency table optimised for the intended expression system, wherein the resulting DNA sequences can optionally be provided with flanking restriction enzyme cleavage sites and conservative base substitutions in order to avoid undesirable restriction enzyme cleavage sites;
f) preparation of the sequences defined in step e) as synthetic DNA by gene synthesis and cloning of the genetic units which code for individual function modules or for a series of a plurality of identical or different function modules into suitable vectors, cloning of the complete modubody by assembly of the individual function modules or function module series in the intended function module sequence and number, wherein a genetic unit coding for the complete modubody can optionally also be cloned directly.

The aim of this construction method, for example the selection of spatially delimited domains, the avoidance of disulphide bridges which stabilise a dimer, and the linking of the individual modules by flexible glycine-serine linkers having a preferred length of from 30 to 40 amino acids, is that the individual modules can behave independently of one another.

The invention relates in addition to a nucleic acid, for example a DNA or RNA, which codes for a fusion polypeptide as described above. The nucleic acid can optionally be present in operative linkage with an expression control sequence, for example a promoter. The invention accordingly relates also to expression vectors which contain a nucleic acid sequence coding for a fusion polypeptide according to the invention and are suitable for the expression of that nucleic acid in a host cell. The host cell can be a prokaryotic host cell, such as a gram-negative bacterium such as *E. coli*, or a gram-positive bacterium such as *B. subtilis*, or a eukaryotic host cell, for example a yeast cell, a fungus cell, an insect cell or a mammalian cell. In order to improve the expression of the nucleic acid in the chosen host cell, it can be optimised in respect of the codon usage in the respective host cell. Corresponding processes are known to the person skilled in the art.

The invention further provides a host cell as indicated above which contains a nucleic acid according to the invention. The nucleic acid can be introduced into the corresponding host cell by known techniques, for example transformation or transfection. For the preparation of the fusion polypeptide according to the invention, the host cell can be cultivated and the fusion polypeptide can be obtained from the cell or from the culture supernatant by methods which are known in principle.

The fusion polypeptides according to the invention can be used, for example, as reagent in a diagnostic or biochemical test, in particular in a test based on immunological methods, for example as control or calibrator reagent or as test reagent for determining an analyte. Detection of the fusion polypeptides according to the invention can take place via the CHX domain(s), for example using isotype- or species-specific recognition reagents, for example secondary antibodies, and/or via non-immunoglobulin recognition domains using specific binding partners for those domains. Corresponding test formats are known to the person skilled in the art.

Furthermore, the fusion polypeptide, the nucleic acid or the host cell according to the present invention can also be used for medical purposes, for example in human or veterinary medicine. Fusion polypeptides can be used, for example, as immunotherapeutic agents, optionally coupled with non-immunoglobulin effector domains, for example radionuclides or toxins. The nucleic acids coding for the fusion polypeptide can be used, for example, as nucleic acid vaccines.

Accordingly, the invention still further provides a pharmaceutical composition which comprises the fusion polypeptide, the nucleic acid or the host cell together with pharmaceutically suitable carrier substances. The pharmaceutical composition can be administered by known methods, as are used, for example, for therapy with antibodies or for DNA vaccination, to a subject, for example a human patient, requiring corresponding therapeutic treatment.

The present invention is to be explained further by means of the following examples.

EXAMPLES

Example 1

Construction, Cloning and Characterisation of a β2-glycoprotein-binding Module (scFv-CAD)

1.1 Construction of the scFv-CAD

The following example describes the construction of a β2-glycoprotein-specific binding module (scFv-CAD) in the form of a synthetic construct.

Portions of the light chain variable region VL (SEQ ID NO: 1) and of the heavy chain variable region VH (SEQ ID NO: 2) of the monoclonal antibody WBCAL-1, which comes from a mouse model of antiphospholipid syndrome, the F1 mouse from New Zealand white X BXSB (Ichikawa et al. (1999), Arthritis and Rheumatism 42:2461), were chosen as structural units for a β2-glycoprotein recognition module and joined with a flexible linker (SEQ ID NO: 3) and flanking sequences to form an artificial protein sequence scFv-RP-CAD-P (SEQ ID NO: 4). This protein sequence was translated, having regard to a codon frequency table, into a nucleic acid sequence optimised for expression in $E.\ coli$, provided with flanking cloning sequences and prepared as an artificial DNA sequence scFv-RP-CAD-N coding for a (β2-glycoprotein recognition module (SEQ ID NO: 5) by gene synthesis. The VL domain extends from amino acid 1-118 in SEQ ID NO: 4, the VH domain extends from amino acid 159-272 in SEQ ID NO: 4.

1.2 Cloning of the scFv-CAD

For the construction, the artificial DNA sequence scFv-RP-CAD-N (SEQ ID NO: 5) described under Example 1.1, which codes for a β2-glycoprotein detection domain, was amplified with the primers RP-CAD01 (SEQ ID NO: 6), RP-CAD02 (SEQ ID NO: 7) by polymerase chain reaction (PCR). The 856 base pair (bp) amplificate was isolated after agarose gel electrophoresis with the QiaExII kit (Qiagen, Hilden). The isolated fragment was first digested with the restriction enzyme HindIII and then subjected to a BgIII partial digestion. The restriction fragments were ligated with the plasmid pQE-80L (Qiagen, Hilden), which was digested with the compatible enzymes BamHI and HindIII, and transformed into $E.\ coli$ strain NovaBlue (Merck, Nottingham). The transformation batch was plated out on LB agar plates supplemented with 50 µg/ml/ml of carbenicillin and incubated overnight (o.n.) (16-20 h) at 36° C. Single colonies of the resulting $E.\ coli$ strain CAD-pQE80-NovaBlue were propagated (36° C., o.n.) on a shaker at 180 revolutions per minute (rpm) in LB medium supplemented with 50 µg/ml of carbenicillin (LB-Carb). Stock cultures for freezing were prepared from the single clone cultures. In each case 1 ml of the single clone cultures was used for plasmid preparation. The isolated plasmids were analysed by EcoRI/HindIII digestion. Clones with an expected 901 bp fragment were investigated further by induction analysis. To that end, the chosen single clones were grown in LB-Carb and, at an O.D. 500 of from 0.5 to 1.0, induced to expression of the protein coded for by the cloned DNA fragment by addition of one culture volume of LB-Carb, 1 mM isopropyl thiogalactoside (IPTG) and cultivated for 16 hours (h) at 36° C., 180 rpm. The induction cells were lysed in sodium dodecyl sulfate (SDS)-containing buffer, proteins were separated by SDS-polyacrylamide gel electrophoresis (PAGE). In the Western blot, the expression of an expected 30 kDa scFv-CAD protein was detected by detection with an anti-RGS-6xHis peroxidase-coupled antibody (Qiagen, Hilden). The correct cloning was confirmed by sequencing.

1.3 Expression of the scFv-CAD $E.\ coli$ strain CAD-pQE80-NovaBlue transformed under 1.2 with the expression construct was grown in LB-Carb medium at 36° C. to an O.D. 500 of from 0.5 to 1.0 and induced to synthesis of the scFv-CAD by addition of IPTG. The induced culture was cultivated at 36° C. for 4 hours to overnight. The induction cells were harvested and lysed after lysozyme treatment in an 8 M urea-containing Tris-HCl-sodium chloride buffer (TBS). Expressed scFv-CAD was purified to homogeneity by a combination of affinity and ion-exchange chromatography. The scFv-CAD protein is visible in the form of a 30 kDa band in the Coomassie blue-stained SDS-polyacrylamide gel. The enhancement of the β2-glycoprotein-binding activity is associated with the purification of the 30 kDa band.

1.4 Characterisation of the scFv-CAD

The binding specificity of the scFv-CAD was tested in an enzyme-linked immunosorbent assay (ELISA) using microtitre plates coated with β2-glycoprotein or with bovine serum albumin (BSA). The stability of the scFv-CAD to heat stress was investigated on suitable dilutions of the scFv-CAD.

1.4.1 Binding Specificity of the scFv-CAD

In order to determine whether scFv-CAD possesses a specific β2-glycoprotein-binding activity, the purified protein module was tested by immunoassays. To that end, serial dilutions of scFv-CAD were applied to microtitre plates of the anti-β2-glycoprotein assay coated with β2-glycoprotein (ORG 521, ORGENTEC Diagnostika GmbH, Mainz) and, for control of the binding specificity, to BSA-coated plates and incubated for 30 minutes at 20-25° C. The microtitre plates were washed and the binding of scFv-CAD was determined using a peroxidase-labelled RGS-6X-His antibody (Qiagen, Hilden) and a tetramethylbenzidine (TMB) colour reaction by measurement of the O.D. 450. As shown in FIG.

2, specific binding to β2-glycoprotein was detected at a concentration of the scFv-CAD of only 19 ng/ml. The comparison of the level of reaction of the scFv-CAD serial dilutions in the binding to β2-glycoprotein- and BSA-coated microtitre plates shows that no non-specific binding occurs in the concentration range 0.019-10 µg/ml scFv-CAD.

1.4.2 Temperature Stability of the scFv-CAD

Figure 3A:
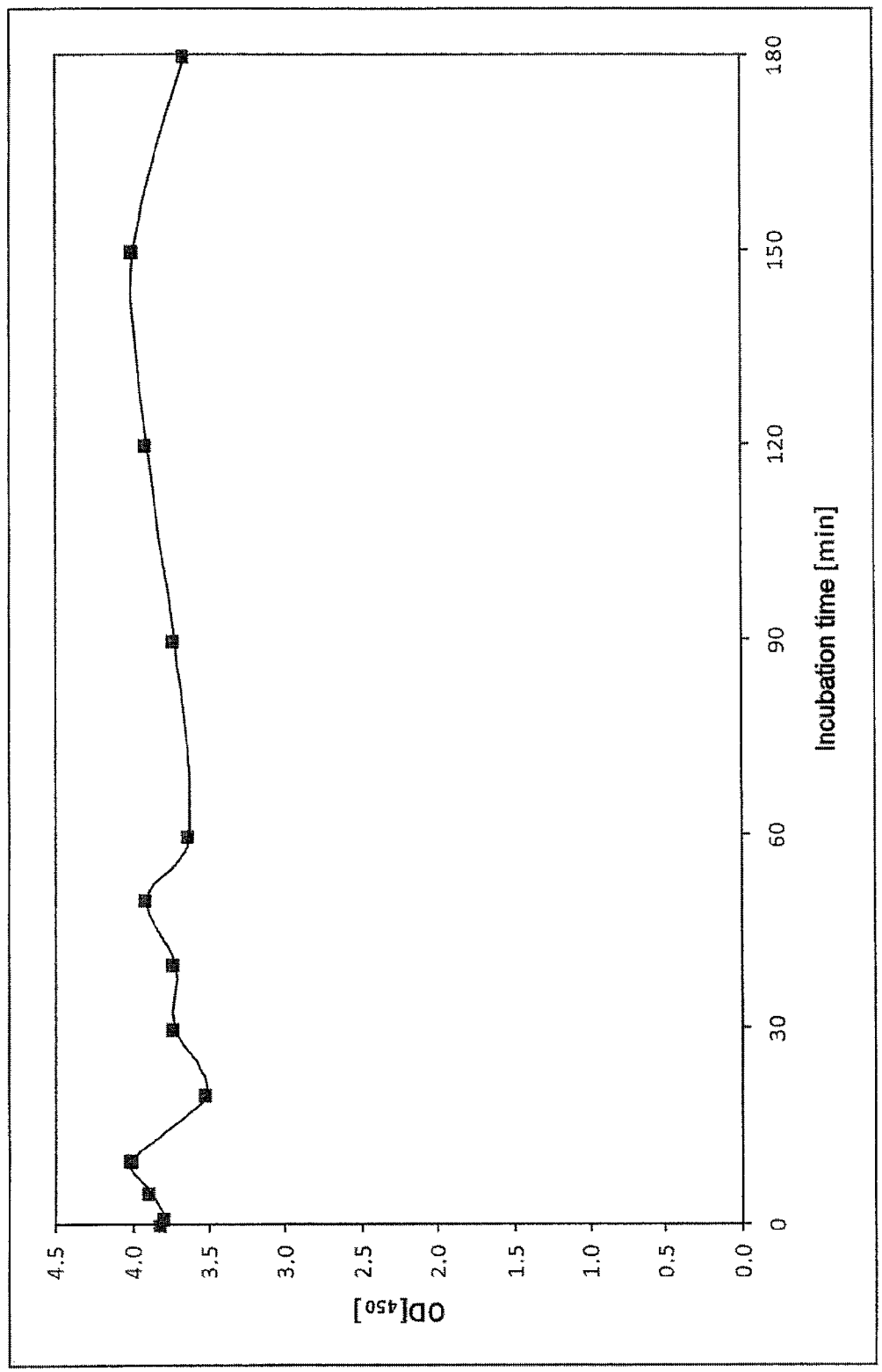

In order to investigate the influence of temperature stress on the specific β2-glycoprotein-binding activity of the scFv-CAD, the purified protein module in a concentration of 5 µg/ml was exposed to a temperature of 50° C. over a period of 0-180 minutes. Binding of the scFv-CAD to β2-glycoprotein was determined in an immunoassay as described under 1.4.1. As shown in FIG. 3A, the scFv-CAD module diluted in calibrator dilution medium was found to be resistant to a temperature of 50° C. for 3 hours.

Figure 3B:
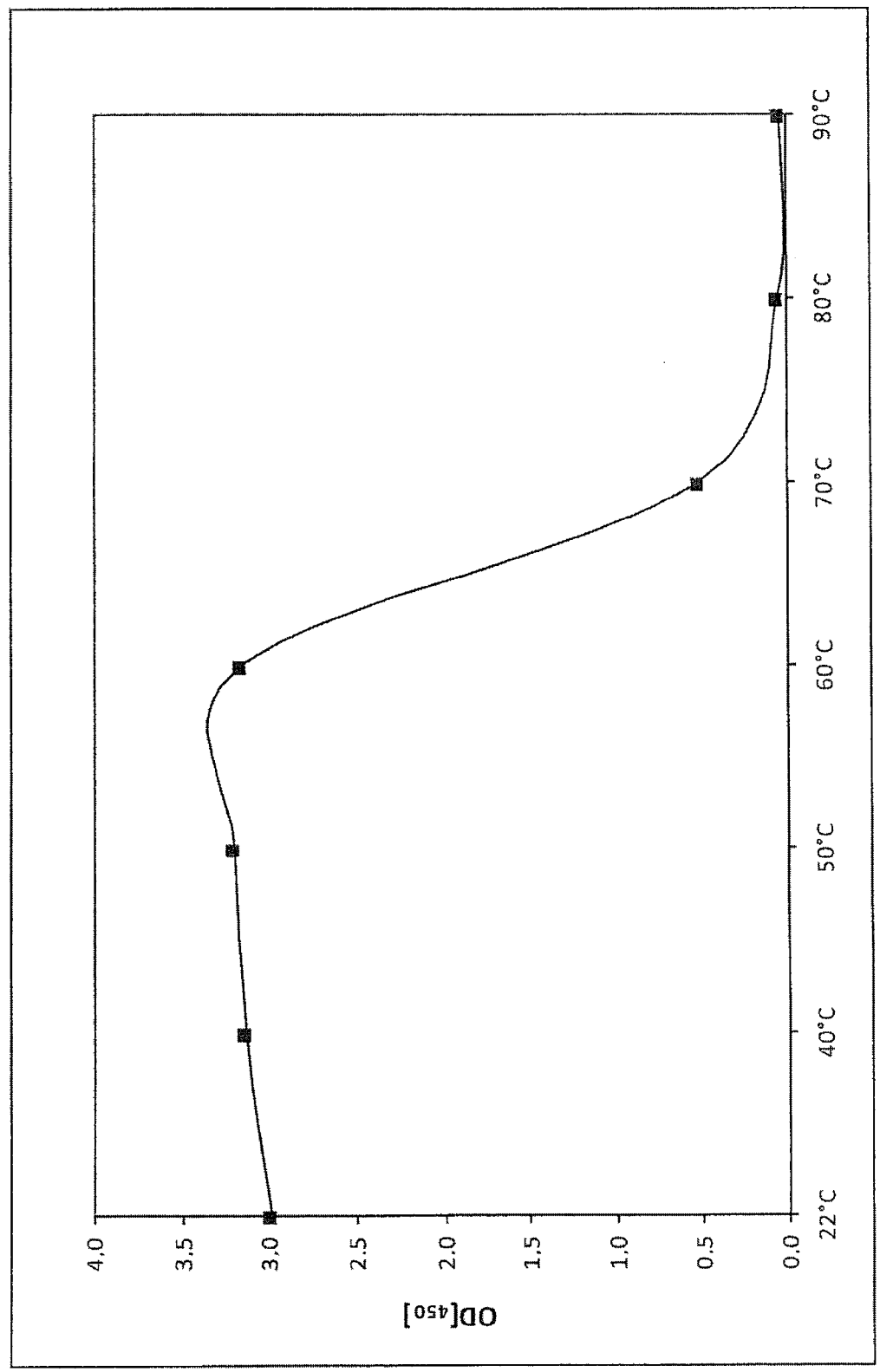

In order to determine the inactivation temperature of the scFv-CAD, the purified protein module in a concentration of 5 µg/ml in calibrator dilution medium was exposed to a series of temperatures of from 20° C. to 90° C. for 10 minutes. The binding of the heat-treated scFv-CAD dilutions to β2-glycoprotein was determined in an immunoassay as described under 1.4.1. As shown in FIG. 3B, the scFv-CAD module was found to be stable up to a temperature of 50° C.; at a temperature of 60° C. and above, marked inactivation occurred.

Example 2

Construction of a Series of Reaction Modules for Modubodies

The following example describes the construction of a series of reaction modules which are derived from domains of the heavy chain constant region of human antibodies. To that end, structurally and functionally delimited domains were derived from protein sequences of the heavy chain of human antibodies of classes IgG, IgA, IgM of known spatial structure. The chosen protein sequences were checked for potential interdomain disulphide bridges. Cysteine positions which outside the chosen domains form disulphide bridges with regions of the intact immunoglobulin were edited from cysteine to serine. At individual glycosylation positions, asparagine was likewise edited to serine. The chosen immunoglobulin domain sequences were joined as structural units for reaction modules with a flexible linker (SEQ ID NO: 3) and flanking sequences to form artificial protein sequences. On the basis of a codon frequency table, these reaction module sequences were translated into a nucleic acid sequence optimised for expression in *E. coli*, provided with flanking cloning sequences and prepared as artificial DNA sequences by gene synthesis.

2.1 Construction of a Human IgG-CH1 Reaction Module

From the Worldwide Protein Data Bank (pdb), (Berman et al. (2003), Nature Structural Biology 10: 980), sequence positions 125-219 were chosen as the representative IgG-CH1 domain from the crystal structure of the Fab fragment of the anti-factor 1× antibody 10c12 on the basis of protein structure data bank entry pdb 3D69H. The chosen IgG-CH1 immunoglobulin domain sequence was joined as structural unit for an IgG-CH1 reaction module with a flexible linker (SEQ ID NO: 3) to form an artificial protein sequence Sc-RP-CH1-G-P (SEQ ID NO: 8) and, having regard to a codon frequency table, translated into a nucleic acid sequence optimised for expression in *E. coli*, additionally provided with flanking cloning sequences (BamHI, HindIII) and prepared as an artificial DNA sequence Sc-RP-CH1-G-N (SEQ ID NO: 9) by gene synthesis. The IgG-CH1 domain extends from amino acid 37-131 in SEQ ID NO: 8.

2.2 Construction of a Human IgG-CH2 Reaction Module

From the crystal structure of the mutated Adcc-strengthened Fc fragment, sequence positions 15-116 were chosen as the representative IgG-CH2 domain on the basis of protein structure data bank entry pdb 2QL1A. The chosen IgG-CH2 immunoglobulin domain sequence was joined as structural unit for an IgG-CH2 reaction module with a flexible linker (SEQ ID NO: 3) to form an artificial protein sequence Sc-RP-CH2-G-P (SEQ ID NO: 10) and, having regard to a codon frequency table, translated into a nucleic acid sequence optimised for expression in *E. coli*, additionally provided with flanking cloning sequences (BamHI/HindIII) and prepared as an artificial DNA sequence Sc-RP-CH2-G-N (SEQ ID NO: 11) by gene synthesis. The IgG-CH2 domain extends from amino acid 37-138 in SEQ ID NO: 10.

2.3 Construction of a Human IgG-CH3 Reaction Module

From the crystal structure of the heavy chain of a human immunoglobulin with a hinge deletion, sequence positions 330-428 were chosen as the representative IgG-CH3 domain on the basis of protein structure data bank entry pdb 1 MCO_H (GI: 494350). The chosen IgG-CH3 immunoglobulin domain sequence was joined as structural unit for an IgG-CH3 reaction module with a flexible linker (SEQ ID NO: 3) to form an artificial protein sequence Sc-RP-CH3-G-P (SEQ ID NO: 12) and, having regard to a codon frequency table, translated into a nucleic acid sequence optimised for expression in *E. coli*, additionally provided with flanking cloning sequences (BamHI/HindIII) and prepared as an artificial DNA sequence Sc-RP-CH3-G-N (SEQ ID NO: 13) by gene synthesis. The IgG-CH3 domain extends from amino acid 37-135 in SEQ ID NO: 12.

2.4 Construction of a Human IgA-CH2 Reaction Module

From a structural model of human IgA, which was derived on the basis of neutron scattering in solution and homology modelling (Boehm et al. (1999) J. Mol. Biol. 286: 1421-1447), sequence positions 126-222 (corresponding to UNIPROT P01876) were chosen as the representative IgA-CH2 domain from protein structure data bank entry pdb 1IGA on the basis of the spatial structure of the heavy chain of human IgA1. At positions 182, 192, cysteine was edited to serine. The chosen and edited IgA-CH2 immunoglobulin domain sequence was joined as structural unit for an IgA-CH2 reaction module with a flexible linker (SEQ ID NO: 3) to form an artificial protein sequence Sc-RP-CH2-A-P (SEQ ID NO: 14) and, having regard to a codon frequency table, translated into a nucleic acid sequence optimised for expression in *E. coli*, additionally provided with flanking cloning sequences (BamHI/HindIII) and prepared as an artificial DNA sequence Sc-RP-CH2-A-N (SEQ ID NO: 15) by gene synthesis. The IgA-CH2 domain extends from amino acid 37-133 in SEQ ID NO: 14.

2.5 Construction of a Human IgA-CH3 Reaction Module

From protein structure data bank entry PDB 1IGA, sequence positions 227-331 (corresponding to UNIPROT P01876) were chosen as the representative IgA-CH3 domain on the basis of the spatial structure of the heavy chain of human IgA1. The chosen IgA-CH3 immunoglobulin domain sequence was joined as structural unit for an IgA-CH3 reaction module with a flexible linker (SEQ ID NO: 3) to form an artificial protein sequence sc-RP-CH3-A-P (SEQ ID NO: 16) and, having regard to a codon frequency table, translated into a nucleic acid sequence optimised for expression in *E. coli*, additionally provided with flanking cloning sequences (BamHI/HindIII) and prepared as an artificial DNA sequence sc-RP-CH3-A-N (SEQ ID NO: 17) by gene synthesis. The IgA-CH3 domain extends from amino acid 37-141 in SEQ ID NO: 16.

2.6 Construction of a Human IgM-CH2 Reaction Module

From a structural model of human IgM which was derived on the basis of X-ray scattering in solution and modelling (Perkins et al. (1991) J. Mol. Biol. 221:1345-1366), sequence positions 106-217 (corresponding to UNIPROT P01871) were chosen as the representative IgM-CH2 domain from protein structure data bank entry pdb 2rcj on the basis of the spatial structure of the heavy chain of human IgM and were edited. At position 214, cysteine was edited to serine; at position 109, asparagine was edited to serine. The chosen and edited IgM-CH2 immunoglobulin domain sequence was joined as structural unit for an IgM-CH2 reaction module with a flexible linker (SEQ ID NO: 3) to form an artificial protein sequence Sc-RP-CH2-M-P (SEQ ID NO: 18) and, having regard to a codon frequency table, translated into a nucleic acid sequence optimised for expression in E. coli, additionally provided with flanking cloning sequences (BamHI/HindIII) and prepared as an artificial DNA sequence Sc-RP-CH2-M-N (SEQ ID NO: 19) by gene synthesis. The IgM-CH2 domain extends from amino acid 37-148 in SEQ ID NO: 18.

2.7 Construction of a Human IgM-CH3 Reaction Module

From protein structure data bank entry pdb 2rcj, sequence positions 218-323 (corresponding to UNIPROT P01871) were chosen as the representative IgM-CH3 domain on the basis of the spatial structure of the heavy chain of human IgM and were edited. At position 291, cysteine was edited to serine; at positions 272 and 279, asparagine was edited to serine. The chosen and edited IgM-CH3 immunoglobulin domain sequence was joined as structural unit for an IgM-CH3 reaction module with a flexible linker (SEQ ID NO: 3) to form an artificial protein sequence Sc-RP-CH3-M-P (SEQ ID NO: 20) and, having regard to a codon frequency table, translated into a nucleic acid sequence optimised for expression in E. coli, additionally provided with flanking cloning sequences (BamHI/HindIII) and prepared as an artificial DNA sequence Sc-RP-CH3-M-N (SEQ ID NO: 21) by gene synthesis. The IgM-CH3 domain extends from amino acids 37-142 in SEQ ID NO: 20.

2.8 Construction of a Human IgM-CH4 Reaction Module

From protein structure data bank entry pdb 2rcj, sequence positions 324-452 (corresponding to UNIPROT P01871) were chosen as the representative IgM-CH3 domain on the basis of the spatial structure of the heavy chain of human IgM and were edited. At position 451, cysteine was edited to serine; at position 439, asparagine was edited to serine. The chosen and edited IgM-CH3 immunoglobulin domain sequence was joined as structural unit for an IgM-CH3 reaction module with a flexible linker (SEQ ID NO: 3) to form an artificial protein sequence Sc-RP-CH4-M-P (SEQ ID NO: 22) and, having regard to a codon frequency table, translated into a nucleic acid sequence optimised for expression in E. coli, additionally provided with flanking cloning sequences (BamHI/HindIII) and prepared as an artificial DNA sequence Sc-RP-CH4-M-N (SEQ ID NO: 23) by gene synthesis. The IgM-CH4 domain extends from amino acid 37-165 in SEQ ID NO: 22.

2.9 Construction of a Monovalent Human IgG-CH3-Knob02 Reaction Module

From the crystal structure of the heavy chain of a human immunoglobulin with a hinge deletion, sequence positions 330-428 were chosen as the representative IgG-CH3 domain on the basis of protein structure data bank entry pdb 1MCO_H (GI:494350) and were edited. Positions of amino acid residues whose side chains form contacts at the interface of $IgG_1$-CH3 dimers (Ridgway J. B. B. et al. (1996), Protein Engineering, 9: 617-621) were so modified that no dimerisation of the IgG-CH3 domain can take place. At positions 351 and 379, threonine was edited to tyrosine; at position 390, phenylalanine was edited to tyrosine. The chosen and edited IgG-CH3 immunoglobulin domain sequence was joined as structural unit for an IgG-CH3-Knob02 reaction module with a flexible linker (SEQ ID NO: 3) to form an artificial protein sequence Sc-RP-CH3-G-Knob02-P (SEQ ID NO: 32) and, having regard to a codon frequency table, translated into a nucleic acid sequence optimised for expression in E. coli, additionally provided with flanking cloning sequences (BamHI/HindIII) and prepared as an artificial DNA sequence Sc-RP-CH3-G-Knob02-N (SEQ ID NO: 33) by gene synthesis. The IgG-CH3-Knob02 domain extends from amino acid 37-135 in SEQ ID NO: 32.

Example 3

The Single-chain CAD-IgG-CH3 Modubody 3.1 Construction and Cloning of the Single-chain CAD-IgG-CH3 Modubody The following example describes the construction and cloning of the β2-glycoprotein-specific modubody CAD-IgG-CH3 provided with a human IgG-CH3 detection domain.

For the construction of the CAD-IgG-CH3 modubody, the modules scFv-CAD (Example 1) and IgG-CH3 (Example 2.3) were assembled by restriction digestion and ligation in the domain sequence VL-linker-VH-linker-IgG-CH3 to form a CAD-IgG-CH3 coding sequence (SEQ ID NO: 26). To that end, the synthetic IgG-CH3 reaction module Sc-RP-CH3-G-N corresponding to sequence SEQ ID NO: 13 and described under Example 2.3 was amplified with the primers CH05 (SEQ ID NO: 24) and CH04 (SEQ ID NO: 25) by PCR. The 443 by amplificate was isolated after agarose gel electrophoresis with the QiaExII kit (Qiagen, Hilden). The isolated fragment was first digested with the restriction enzymes BclI and HindIII. The restriction fragments were ligated with the CAD-scFv-pQE80 vector construct described under Example 1, which was digested with the compatible enzymes BamHI and HindIII, and transformed into E. coli strain NovaBlue (Merck, Nottingham). The transformation batch was plated out on LB agar plates supplemented with carbenicillin (50 µg/ml) and incubated o.n. at 36° C. Single colonies of the resulting E. coli strain CAD-IgG-CH3-pQE80-NovaBlue were propagated (36° C., o.n., 180 rpm) in LB-Carb medium. Stock cultures for freezing were prepared from the single clone cultures, in each case 1 ml of the single clone cultures was used for plasmid preparation. The isolated plasmids were analysed by EcoRI/HindIII digestion. Clones with an expected 1312 by fragment were investigated further by induction analysis. To that end, the chosen single clones were grown in LB-Carb and, at an O.D. 500 of from 0.5 to 1.0, induced to expression of the recombinant protein by addition of one culture volume of LB-Carb supplemented with 1 mM IPTG, and cultivated for 16 hours at 36° C., 180 rpm. The induction cells were lysed in SDS sample buffer, proteins were separated by SDS-PAGE. In the Western blot, the expression of the expected 44 kDa CAD-IgG-CH3 modubody was detected by detection with an anti-RGS-6xHis peroxidase-coupled antibody (Qiagen, Hilden). The correct cloning was confirmed by sequencing.

3.2 Expression and Purification of the Single-chain CAD-IgG-CH3 Modubody

The following example describes the expression and purification of the β2-glycoprotein-specific modubody CAD-IgG-CH3 provided with a human IgG-CH3 detection domain.

*E. coli* strain CAD-IgG-CH3-pQE80-NovaBlue transformed under 3.1 with the expression construct was grown in LB-Carb medium at 36° C. to an O.D. 500 of from 0.5 to 1.0 and induced to synthesis of the CAD-IgG-CH3 modubody by addition of IPTG. The induced culture was cultivated at 36° C. for 4 hours to overnight. The induction cells were harvested and lysed after lysozyme treatment in an 8 M urea-containing TBS buffer. Expressed CAD-IgG-CH3 modubodies were purified to homogeneity by a combination of affinity and ion-exchange chromatography. A 44 kDa band is visible in the Coomassie blue-stained SDS-polyacrylamide gel. The enhancement of the β2-glycoprotein-binding activity and a reactivity with a peroxidase-coupled antihuman IgG secondary antibody (Jackson Immunoresearch) is associated with the purification of the 44 kDa band.

3.3 Characteristics of the Single-chain CAD-IgG-CH3 Modubody

The following example describes the characterisation of the β2-glycoprotein-specific modubody CAD-IgG-CH3 provided with a human IgG-CH3 detection domain in relation to specific antigen recognition, specific detectability via an antihuman IgG secondary antibody, and stability to elevated temperatures, drying and freeze-thaw cycles.

3.3.1 Calibrator Function of the CAD-IgG-CH3 Modubody

In order to determine whether the CAD-IgG-CH3 modubody has retained the β2-glycoprotein-binding activity of the scFv-CAD and binding to the antigen can be detected specifically via an antihuman IgG secondary antibody, purified CAD-IgG-CH3 preparations were investigated in an anti-β2-glycoprotein immunoassay. The purified CAD-IgG-CH3 modubody was applied in serial dilutions with concentrations of 0 µg/ml, 0.31 µg/ml, 0.62 µg/ml, 1.25 µg/ml, 2.5 µg/ml, 5 µg/ml, 10 µg/ml, 20 µg/ml in calibrator dilution medium to microtitre plates coated with β2-glycoprotein. The antigen-binding activity was determined under the incubation conditions provided for the anti-β2-glycoprotein assay (ORG 521, ORGENTEC GmbH, Mainz) using an antihuman IgG peroxidase-labelled secondary antibody in a concentration of 80 ng/ml. FIG. 4 shows the variation in the OD 450 nm determined under the chosen reaction conditions in dependence on the concentration. Under the chosen reaction conditions, the CAD-IgG-CH3 modubody was detected at a concentration of 5 µg/ml with an O.D. 450 of 2.2.

3.3.2 Stability of the CAD-IgG-CH3 Modubody

In order to characterise the robustness of the CAD-IgG-CH3 modubody, dilutions in calibrator dilution medium were exposed to the stress factors of 50° C. heat stress, elevated storage temperature at 36° C., dryness and repeated freeze-thaw cycles. The β2-glycoprotein-binding activity and the detectability with an anti-hu IgG peroxidase-labelled secondary antibody (Jackson Immunoresearch) were determined in comparison with untreated samples.

3.3.2.1 Stability of the CAD-IgG-CH3 Modubody to Heat Stress

The stability to heat stress was investigated as follows: dilutions of the CAD-IgG-CH3 modubody in calibrator dilution medium in concentrations of 0 µg/ml, 0.31 µg/ml, 0.62 µg/ml, 1.25 µg/ml, 2.5 µg/ml, 5 µg/ml, 10 µgl/ml, 20 µg/ml were incubated for 60 minutes and 90 minutes at 50° C. and investigated in an anti-β2-glycoprotein immunoassay in comparison with a dilution series stored at room temperature. The β2-glycoprotein-binding activity was determined under the incubation conditions provided for the anti-β2-glycoprotein assay (ORG 521, ORGENTEC GmbH, Mainz) using an antihuman IgG peroxidase-labelled secondary antibody in a concentration of 80 ng/ml. FIG. 5 shows the variation in the OD 450 nm determined under the chosen reaction conditions for the dilution series incubated for 60 and 90 minutes at 50° C. in comparison with the dilution series stored at room temperature. Under the chosen reaction conditions, the function of the CAD-IgG-CH3 modubody in dilutions in the concentration range from 0.31 µg/ml to 20 µg/ml was not impaired by 50° C. temperature stress for 60 minutes or 90 minutes.

3.3.2.2 Stability of the CAD-IgG-CH3 Modubody to Storage at 36° C.

Figure 6:
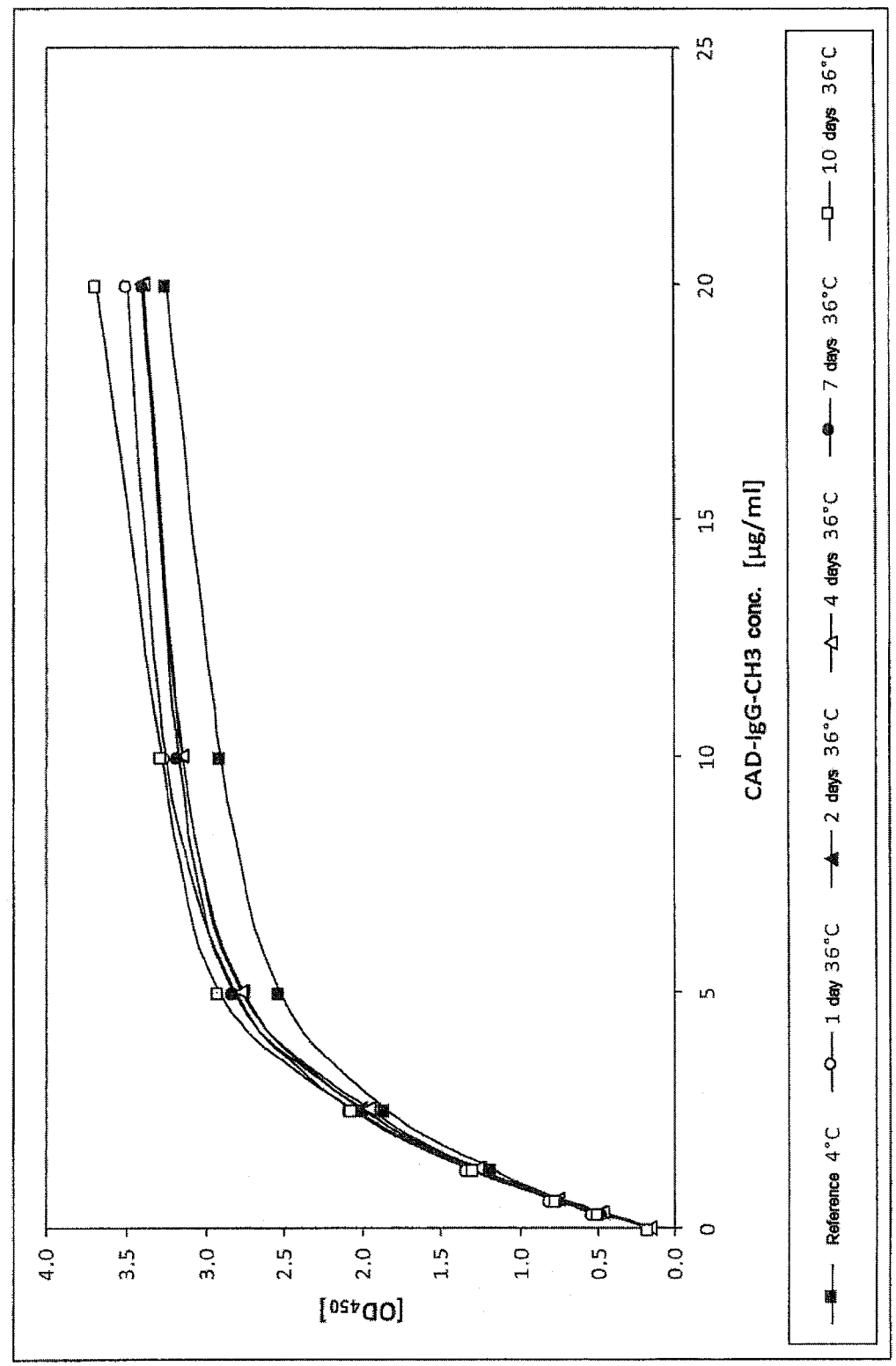

The stability to elevated storage temperature was investigated as follows: dilutions of the CAD-IgG-CH3 modubody in concentrations of 0 µg/ml, 0.31 µg/ml, 0.62 µg/ml, 1.25 µg/ml, 2.5 µg/ml, 5 µg/ml, 10 µg/ml, 20 µg/ml in calibrator dilution medium were incubated for 1, 2, 4, 7, 10 days at 36° C. and investigated in an anti-β2-glycoprotein immunoassay in comparison with a dilution series stored at 4° C. The β2-glycoprotein-binding activity was determined under the incubation conditions provided for the anti-β2-glycoprotein assay (ORG 521, ORGENTEC GmbH, Mainz) using an antihuman IgG peroxidase-labelled secondary antibody in a concentration of 80 ng/ml. FIG. 6 shows the variation in the OD 450 nm determined under the chosen reaction conditions for the dilution series stored for 1, 2, 4, 7, 10 days at 36° C. in comparison with the dilution series stored at 4° C. Under the chosen reaction conditions, the function of the CAD-IgG-CH3 modubody in dilutions in the concentration range from 0.31 µg/ml to 20 µg/ml was not impaired by storage at 36° C. over a period of ten days.

3.3.2.3 Stability of the CAD-IgG-CH3 Modubody to Drying

Figure 7:
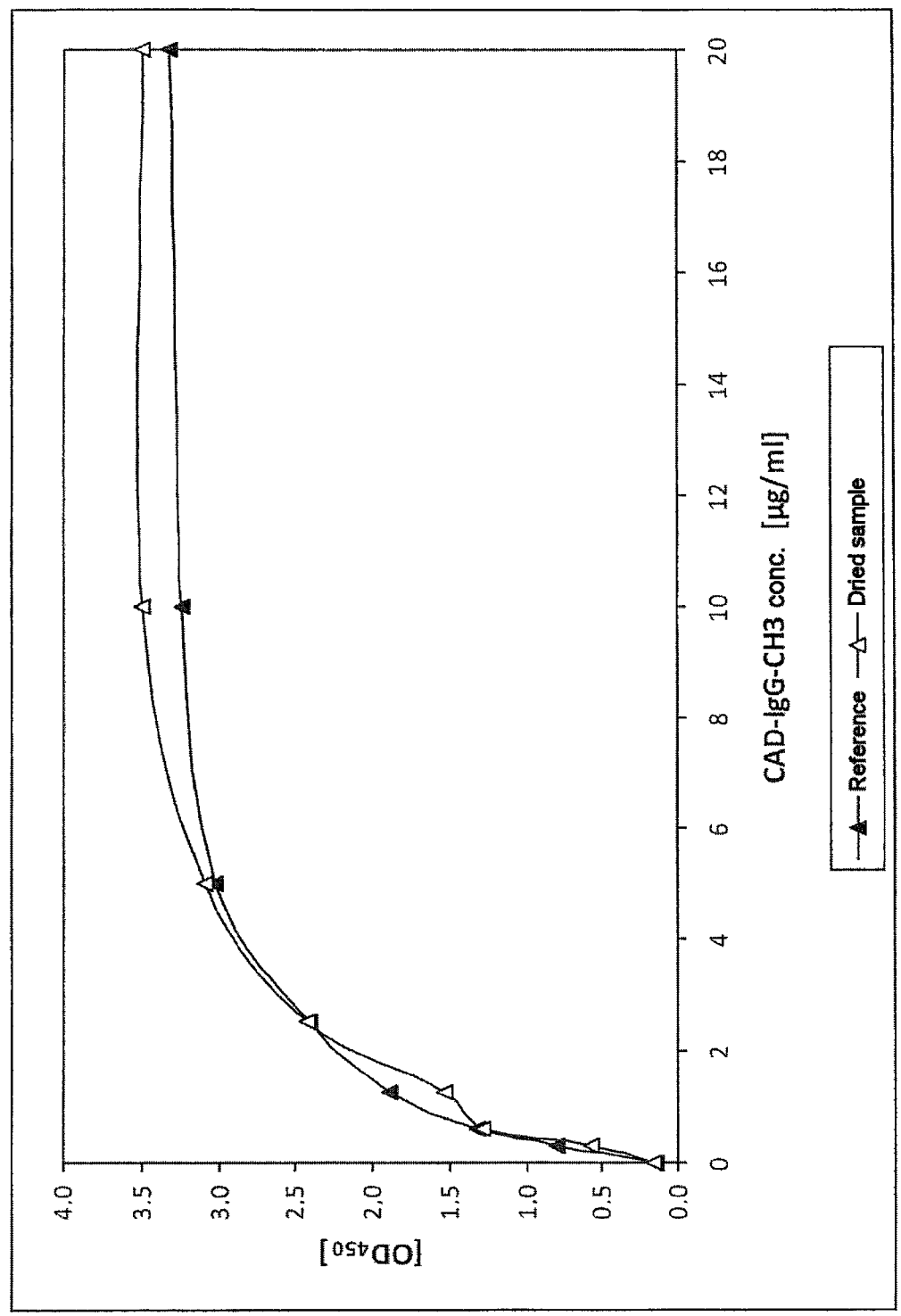

The stability to drying was investigated as follows: dilutions of the CAD-IgG-CH3 modubody in calibrator dilution medium in 50 µl portions in concentrations of 0 µg/ml, 3.1 µg/ml, 6.21 µg/ml, 12.5 µg/ml, 25 µg/ml, 50 µg/ml, 100 µg/ml, 200 µg/ml were dried in vacuo at 22° C. in a Speedvak. The dried samples were resolubilised with 450 µl of calibrator dilution medium and 50 µl of water to give a dilution series with concentrations of 0 µg/ml, 0.31 µg/ml, 0.62 µg/ml, 1.25 µg/ml, 2.5 µg/ml, 5 µg/ml, 10 µg/ml, 20 µg/ml and were investigated in an anti-β2-glycoprotein-cardiolipin immunoassay in comparison with an untreated dilution series. The β2-glycoprotein-binding activity was determined under the incubation conditions provided for the anti-cardiolipin-β2-glycoprotein assay (ORG 515, ORGENTEC GmbH, Mainz) using an antihuman IgG peroxidase-labelled secondary antibody in a concentration of 80 ng/ml. FIG. 7 shows the variation in the OD 450 nm determined under the chosen reaction conditions for the dried samples in comparison with the untreated dilution series. Under the chosen reaction conditions, the function of the CAD-IgG-CH3 modubody in dilutions in the concentration range from 3.1 µg/ml to 200 µg/ml was not impaired by drying.

3.3.2.4 Stability of the CAD-IgG-CH3 Modubody to Freeze-thaw Cycles

Figure 8:
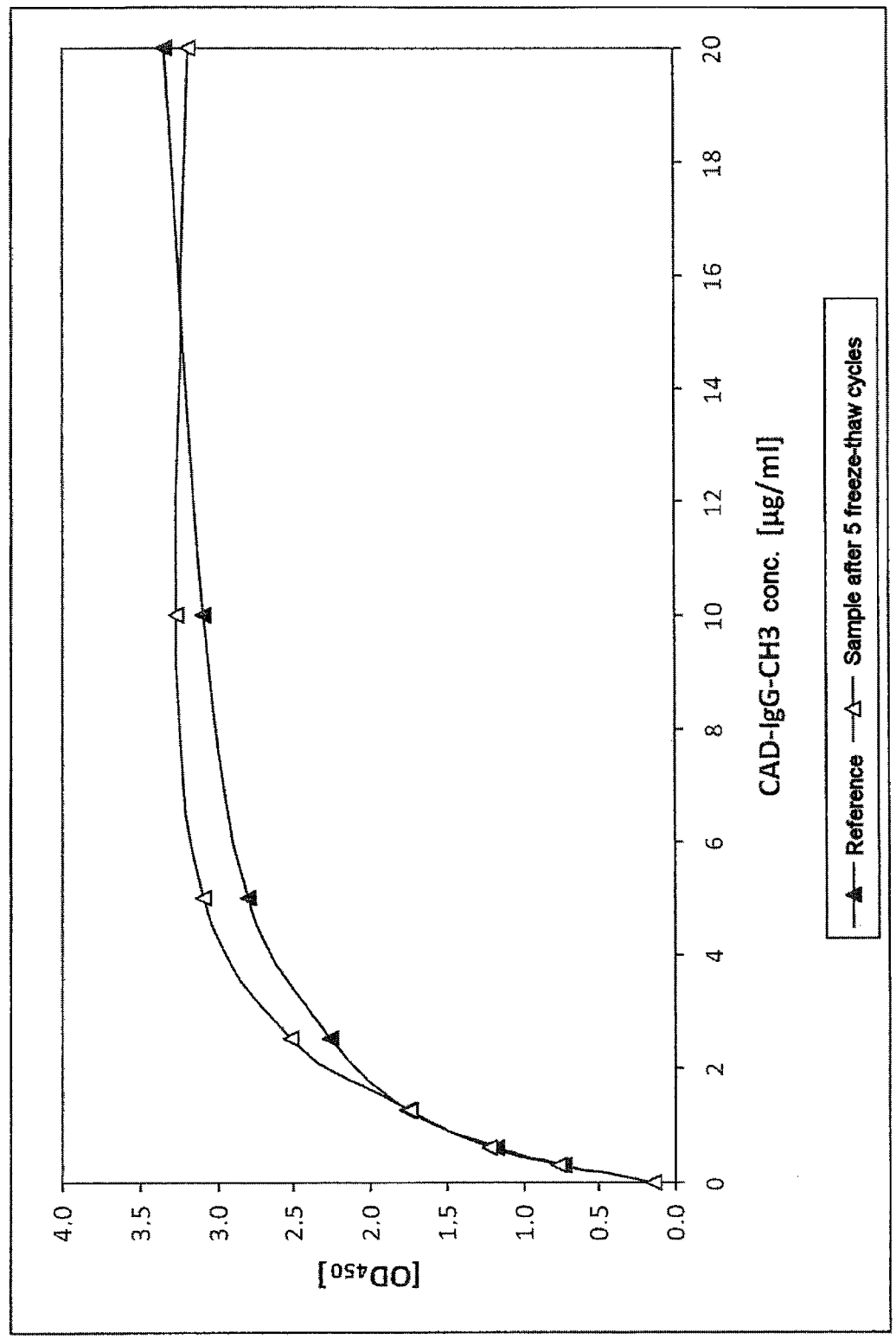

The stability to repeated freeze-thaw cycles was investigated as follows: dilutions of the CAD-IgG-CH3 modubody in calibrator dilution medium in 50 µl portions in concentrations of 0 µg/ml, 3.1 µg/ml, 6.21 µg/ml, 12.5 µg/ml, 25 µg/ml, 50 µg/ml, 100 µg/ml, 200 µg/ml were frozen at −70° C. and thawed again at 37° C. in five repeated freeze-thaw cycles. The samples were then diluted with 450 µl of calibrator dilution medium to give a dilution series with concentrations of 0 µg/ml, 0.31 µg/ml, 0.62 µg/ml, 1.25 µg/ml, 2.5 µg/ml, 5 µg/ml, 10 µg/ml, 20 µg/ml and were investigated in an anti-β2- cardiolipin-glycoprotein immunoassay in comparison with an untreated CAD-IgG-CH3 dilution series. The β2-glycoprotein-binding activity was determined under the incubation conditions provided for the anti-cardiolipin-β2-glycoprotein assay (ORG 515, ORGENTEC GmbH, Mainz) using an anti-human IgG peroxidase-labelled secondary antibody in a concentration of 80 ng/ml. FIG. 8 shows the variation in the OD 450 nm determined under the chosen reaction conditions for the repeatedly frozen and thawed samples in comparison with the untreated dilution series. Under the chosen reaction conditions, the function of the CAD-IgG-CH3 modubody in the concentration range from 3.1 µg/ml to 200 µg/ml was not impaired by repeated freeze-thaw cycles.

Example 4

The Single-chain CAD-IgG-CH2 Modubody 4.1 Construction and Cloning of the Single-chain CAD-IgG-CH2 Modubody The following example describes the construction and cloning of the β2-glycoprotein-specific modubody CAD-IgG-CH2 provided with a monomeric human IgG-CH2 detection domain. For the construction of the CAD-IgG-CH2 modubody, the modules scFv-CAD (Example 1) and IgG-CH2 (Example 2.2) were assembled by restriction digestion and ligation in the domain sequence VL-linker-VH-linker-IgG-CH2 to form a CAD-IgG-CH2 coding sequence (SEQ ID NO: 27). To that end, the synthetic IgG-CH2 reaction module Sc-RP-CH2-G-N corresponding to sequence SEQ ID NO: 11 and described under Example 2.2 was amplified with the primers CH03 (SEQ ID NO: 28) and CH04 (SEQ ID NO: 25) by PCR. The 443 by amplificate was gel-isolated after agarose gel electrophoresis with the QiaExII kit (Qiagen, Hilden). The gel-isolated fragment was first digested with the restriction enzymes BclI and HindIII. The restriction fragments were ligated with the scFv-CAD-pQE80 vector construct described under Example 1, which was digested with the compatible enzymes BamHI and HindIII, and transformed into *E. coli* strain NovaBlue (Merck, Nottingham). The transformation batch was plated out on LB agar plates supplemented with carbenicillin (50 µg/ml) and incubated overnight at 36° C. Single colonies of the resulting *E. coli* strain CAD-IgG-CH2-pQE80-NovaBlue were propagated (36° C., overnight, 180 rpm) in LB medium supplemented with carbenicillin (50 µg/ml) (LB-Carb.). Stock cultures for freezing were prepared from the single clone cultures, in each case 1 ml of the single clone cultures was used for plasmid preparation. The isolated plasmids were analysed by EcoRI/HindIII digestion. Clones with an expected 1321 by fragment were investigated further by induction analysis. To that end, the chosen single clones were grown in LB-Carb. and, at an O.D. 500 of from 0.5 to 1.0, induced to expression of the recombinant protein by addition of one culture volume of LB-Carb. supplemented with 1 mM IPTG, and cultivated for 16 hours at 36° C., 180 rpm. The induction cells were lysed in SDS sample buffer, proteins were separated by SDS-PAGE. In the Western blot, the expression of the expected 44 kDa CAD-IgG-CH2 modubody was detected by detection with an anti-RGS-6xHis peroxidase-coupled antibody (Qiagen, Hilden). The correct cloning was confirmed by sequencing.

4.2 Expression and Purification of the Single-chain CAD-IgG-CH2 Modubody

The following example describes the expression and purification of the β2-glycoprotein-specific modubody CAD-IgG-CH2 provided with a monomeric human IgG-CH2 detection domain.

*E. coli* strain CAD-IgG-CH2-pQE80-NovaBlue transformed under 4.1 with the expression construct was grown in LB-Carb. medium at 36° C. to an O.D. 500 of from 0.5 to 1.0 and induced to synthesis of the CAD-IgG-CH2 modubody by addition of IPTG. The induced culture was cultivated at 36° C. for 4 hours to overnight. The induction cells were harvested and lysed after lysozyme treatment in an 8M urea-containing TBS buffer. Expressed CAD-IgG-CH2 modubodies were purified by Ni-NTA affinity chromatography. A 44 kDa band is visible in the Coomassie blue-stained SDS-polyacrylamide gel. The enhancement of the β2-glycoprotein-binding activity and a reactivity with a peroxidase-coupled antihuman IgG secondary antibody (Jackson Immunoresearch) is associated with the purification of the 44 kDa band.

4.3 Characteristics of the Single-chain CAD-IgG-CH2 Modubody

The following example describes the characterisation of the β2-glycoprotein-specific modubody CAD-IgG-CH2 provided with a monomeric human IgG-CH2 detection domain in relation to specific antigen recognition, specific detectability via an antihuman IgG secondary antibody, and stability to elevated temperatures, drying and freeze-thaw cycles.

4.3.1 Calibrator Function of the CAD-IgG-CH2 Modubody

Figure 9:
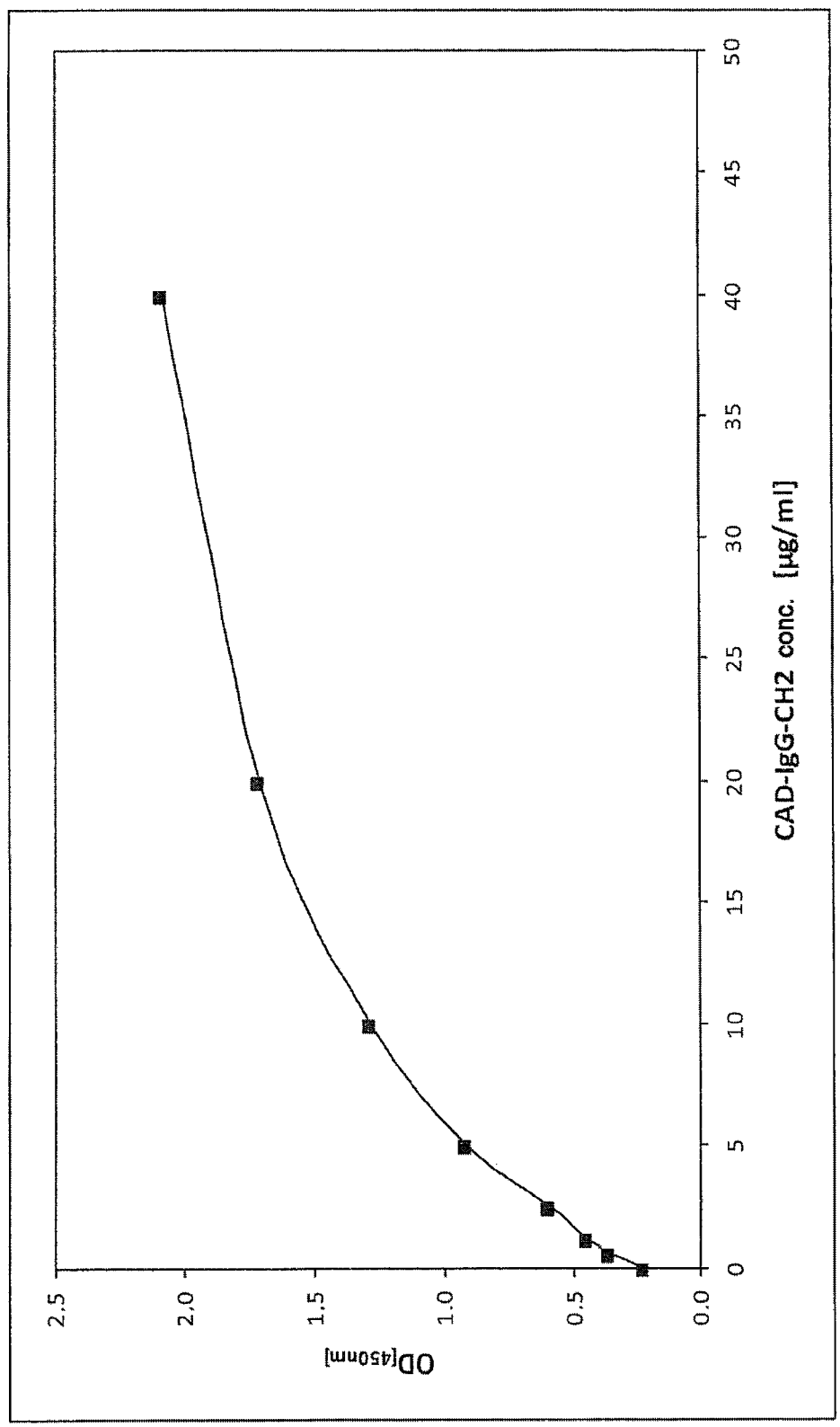

In order to determine whether the CAD-IgG-CH2 modubody has retained the β2-glycoprotein-binding activity of the scFv-CAD and binding to the antigen can be detected specifically via an antihuman IgG secondary antibody, purified CAD-IgG-CH2 preparations were investigated in an anti-cardiolipin/β2-glycoprotein immunoassay. The purified CAD-IgG-CH2 modubody was applied in a dilution series with concentrations of 0 µg/ml, 0.62 µg/ml, 1.25 µg/ml, 2.5 µg/ml, 5 µg/ml, 10 µg/ml, 20 µg/ml, 40 µg/ml in calibrator dilution medium to microtitre plates coated with β2-glycoprotein in complex with cardiolipin. The antigen-binding activity was determined under the incubation conditions provided for the anti-cardiolipin assay (ORG 515, ORGENTEC GmbH, Mainz) using an antihuman IgG peroxidase-labelled secondary antibody (Jackson Immunoresearch) in a concentration of 200 ng/ml. FIG. 9 shows the variation in the OD 450 nm determined under the chosen reaction conditions in dependence on the concentration. Under the chosen reaction conditions, the CAD-IgG-CH2 modubody was detected at a concentration of 20 µg/ml with an O.D. 450 nm of 1.7.

4.3.2 Stability of the CAD-IgG-CH2 Modubody to Drying

Figure 10:
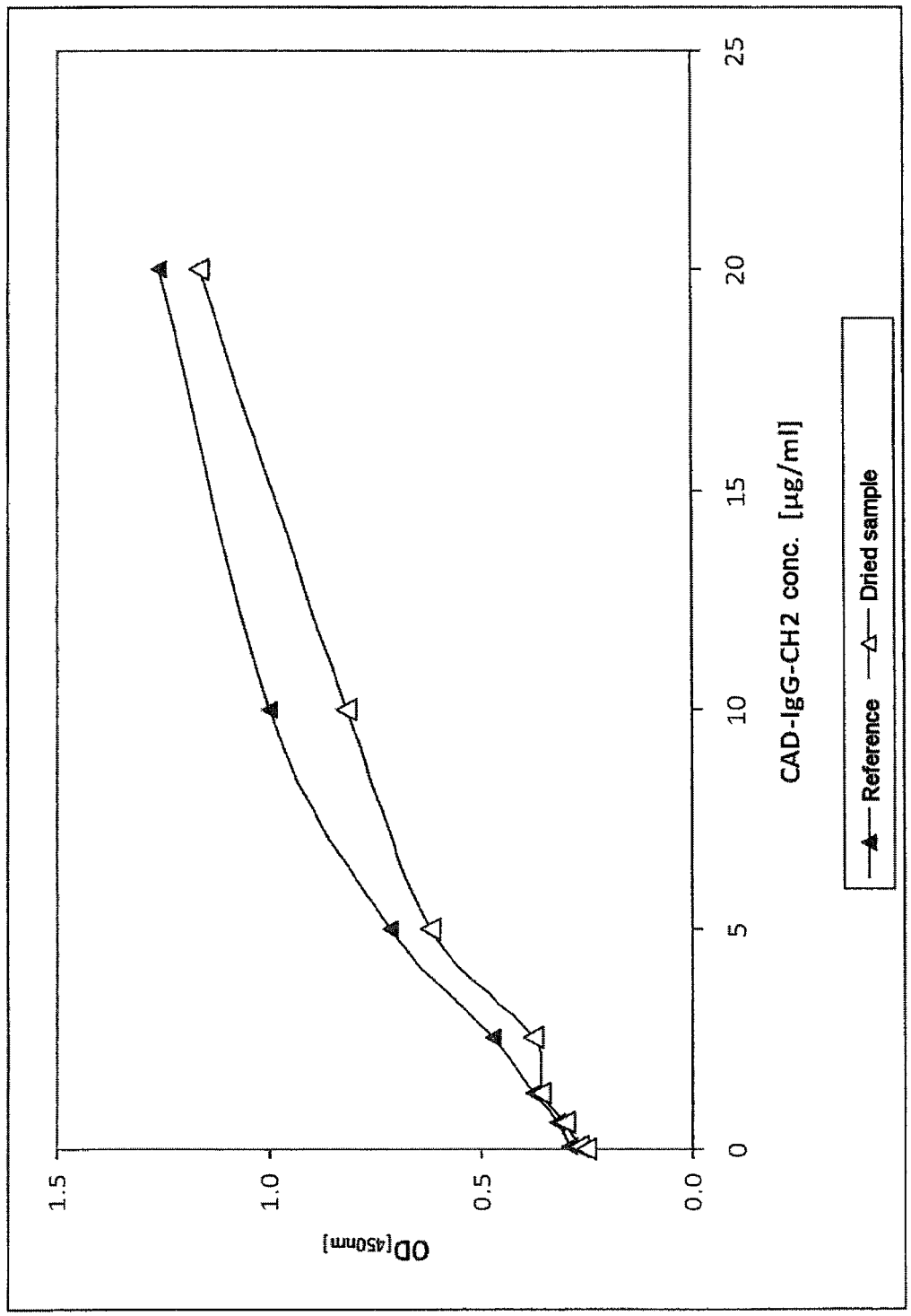

The stability to drying was investigated as follows: dilutions of the CAD-IgG-CH2 modubody in calibrator dilution medium in 50 µl portions in concentrations of 0 µg/ml, 3.1 µg/ml, 6.21 µg/ml, 12.5 µg/ml, 25 µg/ml, 50 µg/ml, 100 µg/ml, 200 µg/ml were dried in vacuo at 22° C. in a Speedvak device. The dried samples were resolubilised with 450 µl of calibrator dilution medium and 50 µl of water to give a dilution series with concentrations of 0 µg/ml, 0.31 µg/ml, 0.62 µg/ml, 1.25 µg/ml, 2.5 µg/ml, 5 µg/ml, 10 µg/ml, 20 µg/ml and in comparison with an untreated dilution series were applied to microtitre plates coated with β2-glycoprotein in complex with cardiolipin. The antigen-binding activity was determined under the incubation conditions provided for the anti-cardiolipin assay (ORG 515, ORGENTEC GmbH, Mainz) using an antihuman IgG peroxidase-labelled secondary antibody (Jackson Immunoresearch) in a concentration of 200 ng/ml. FIG. 10 shows the variation in the OD 450 nm determined under the chosen reaction conditions for the dried samples in comparison with the untreated dilution series. Under the chosen reaction conditions, the function of the CAD-IgG-CH2 modubody in dilutions in the concentration range from 3.1 µg/ml to 200 µg/ml was not impaired by drying.

4.3.3 Stability of the CAD-IgG-CH2 Modubody to Freeze-thaw Cycles

Figure 11:
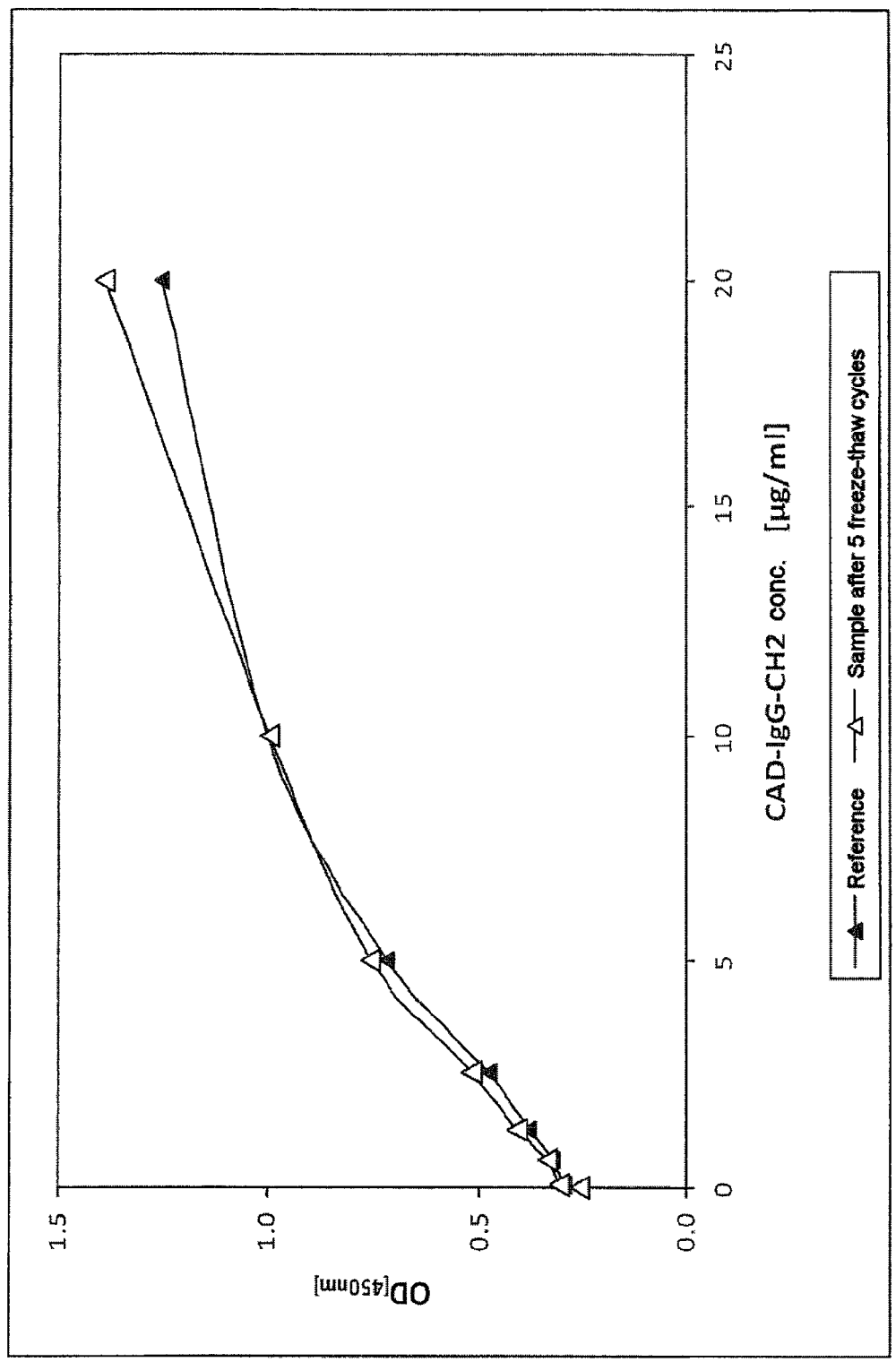

The stability to repeated freeze-thaw cycles was investigated as follows: dilutions of the CAD-IgG-CH2 modubody in calibrator dilution medium in 50 µl portions in concentrations of 0 µg/ml, 3.1 µg/ml, 6.21 µg/ml, 12.5 µg/ml, 25 µg/ml, 50 µg/ml, 100 µg/ml, 200 µg/ml were frozen at −70° C. and thawed again at 37° C. in five repeated freeze-thaw cycles. The samples were then diluted with 450 µl of calibrator dilution medium to give a dilution series with concentrations of 0 µg/ml, 0.31 µg/ml, 0.62 µg/ml, 1.25 µg/ml, 2.5 µg/ml, 5 µg/ml, 10 µg/ml, 20 µg/ml and in comparison with an untreated CAD-IgG-CH2 dilution series were applied to microtitre plates coated with β2-glycoprotein in complex with cardiolipin. The antigen-binding activity was determined under the incubation conditions provided for the anti-cardiolipin assay (ORG 515, ORGENTEC GmbH, Mainz) using an antihuman IgG peroxidase-labelled secondary antibody (Jackson Immunoresearch) in a concentration of 200 ng/ml. FIG. 11 shows the variation in the OD 450 nm determined under the chosen reaction conditions for the repeatedly frozen and thawed samples in comparison with the untreated dilution series. Under the chosen reaction conditions, the function of the CAD-IgG-CH2 modubody in the concentration range from 3.1 µg/ml to 200 µg/ml was not impaired by repeated freeze-thaw cycles.

Example 5

The single-chain Multifunctional CAD-IgM-IgA-IgG Modubody

The single-chain multifunctional modubody CAD-IgM-IgA-IgG contains four function modules in a linear sequence. A β2-glycoprotein recognition domain and a plurality of reaction modules derived from CH3 domains of the heavy chain of human immunoglobulins IgM, IgA and IgG are linked via peptide linkers. Detection of the CAD-IgM-IgA-IgG modubody can thus take place via different isotype-specific secondary antibodies.

5.1 Construction and Cloning of the Single-chain CAD-IgM-IgA-IgG Modubody

The following example describes the construction and cloning of the β2-glycoprotein-specific modubody CAD-IgM-IgA-IgG provided with human IgM-, IgG- and IgA-CH3 detection domains.

For the construction of the CAD-IgM-IgA-IgG modubody, the modules scFv-CAD (Example 1), IgM-CH3 (Example 2.7), IgA-CH3 (Example 2.5) and IgG-CH3 (Example 2.3) were assembled by restriction digestion and ligation in the domain sequence VL-linker-VH-linker-IgM-CH3-linker-IgA-CH3-linker-IgG-CH3 to form a CAD-IgM-IgA-IgG coding sequence (SEQ ID NO: 29). To that end, the reaction modules IgM-CH3, IgA-CH3 and IgG-CH3 were inserted into the CAD-scFv-pQE80 vector construct described under Example 1 in an iterative process comprising restrictions of vector constructs and insert ligations. In the first construction step, the synthetic IgM-CH3 reaction module Sc-RP-CH3-M-N corresponding to sequence SEQ ID NO: 21 and described under Example 2.7 was amplified with the primers CH09 (SEQ ID NO: 30) and CH04 (SEQ ID NO: 25) by PCR. The 455 by amplificate was gel-isolated after agarose gel electrophoresis with the QiaExII kit (Qiagen, Hilden). The gel-isolated fragment was digested with the restriction enzymes BamI and HindIII. The restriction fragments were ligated with the scFv-CAD-pQE80 vector construct described under Example 1, which was digested with the compatible enzymes BamHI and HindIII, and transformed into E. coli strain NovaBlue (Merck, Nottingham) and plated out on LB agar plates supplemented with carbenicillin (50 µg/ml) and incubated overnight at 36° C. Plasmid DNA was isolated from a single clone with correct insert ligation. In a second construction step, the synthetic IgA-CH3 reaction module Sc-RP-CH3-A-N corresponding to sequence SEQ ID NO: 17 and described under Example 2.5 was amplified with the primers CH07(SEQ ID NO: 31) and CH04 (SEQ ID NO: 25) by PCR. The 452 by amplificate was gel-isolated after agarose gel electrophoresis with the QiaExII kit (Qiagen, Hilden). The gel-isolated fragment was digested with the restriction enzymes BamHI and HindIII. The restriction fragments were ligated with the vector construct isolated in the first construction step, which was digested with the compatible enzymes BamHI and HindIII, and transformed into E. coli strain NovaBlue (Merck, Nottingham) and plated out on LB agar plates supplemented with carbenicillin (50 µg/ml) and incubated overnight at 36° C. Plasmid DNA was isolated from a single clone with correct insert ligation. In a third construction step, the synthetic IgG-CH3 reaction module Sc-RP-CH3-G-N corresponding to sequence SEQ ID NO: 13 and described under Example 2.3 was amplified with the primers CH05 (SEQ ID NO: 24) and CH04 (SEQ ID NO: 25) by PCR. The 434 by amplificate was gel-isolated after agarose gel electrophoresis with the QiaExII kit (Qiagen, Hilden). The gel-isolated fragment was digested with the restriction enzymes BcII and HindIII. The restriction fragments were ligated with the vector construct isolated in the second construction step, which was digested with the compatible enzymes BamHI and HindIII, and transformed into E. coli strain NovaBlue (Merck, Nottingham). The transformation batch was plated out on LB agar plates supplemented with carbenicillin (50 µg/ml) and incubated overnight at 36° C. Single colonies of the resulting E. coli strain CAD-IgM-IgA-IgG-pQE80-NovaBlue were propagated (36° C., overnight, 180 rpm) in LB medium supplemented with carbenicillin (50 µg/ml) (LB-Carb.). Stock cultures for freezing were prepared from the single clone cultures, in each case 1 ml of the single clone cultures was used for plasmid preparation. The isolated plasmids were analysed by EcoRI/HindIII digestion. Clones with an expected 2173 by fragment were investigated further by induction analysis. To that end, the chosen single clones were grown in LB-Carb. and, at an O.D. 500 of from 0.5 to 1.0, induced to expression of the protein coded for by the cloned DNA construct by addition of one culture volume of LB-Carb. supplemented with 1 mM IPTG, and cultivated for 16 hours at 36° C., 180 rpm. The induction cells were lysed in SDS sample buffer, proteins were separated by SDS-PAGE. In the Western blot, the expression of the expected 72 kDa CAD-IgM-IgA-IgG modubody was detected by detection with an anti-RGS-6xHis peroxidase-coupled antibody (Qiagen, Hilden). The correct cloning was confirmed by sequencing.

5.2 Expression and Purification of the Single-chain CAD-IgM-IgA-IgG Modubody

The following example describes the expression and purification of the β2-glycoprotein-specific modubody CAD-IgM-IgA-IgG provided with human IgM-CH3, IgA-CH3 and IgG-CH3 detection domains.

E. coli strain CAD-IgM-IgA-IgG-pQE80-NovaBlue transformed under 5.1 with the expression construct was grown in LB-Carb medium at 36° C. to an O.D. 500 of from 0.5 to 1.0 and induced to synthesis of the CAD-IgM-IgA-IgG modubody by addition of IPTG. The induced culture was cultivated at 36° C. for 4 hours to overnight. The induction cells were harvested and lysed after lysozyme treatment in an 8M urea-containing TBS buffer. Expressed CAD-IgM-IgA-IgG modubodies were purified by affinity chromatography. A 72 kDa band is visible in the Coomassie blue-stained SDS-polyacrylamide gel. The enhancement of the β2-glycoprotein-binding activity and a reactivity with peroxidase-coupled antihuman IgM, IgA and IgG secondary antibodies (Jackson Immunoresearch) is associated with the purification of the 72 kDa band.

5.3 Characteristics of the Single-chain CAD-IgM-IgA-IgG Modubody

The following example describes the characterisation of the β2-glycoprotein-specific modubody CAD-IgM-IgA-IgG provided with human IgM-CH3, IgA-CH3 and IgG-CH3 detection domains in relation to specific antigen recognition, specific detectability via antihuman IgM, IgA and IgG secondary antibodies, and stability to drying and freeze-thaw cycles.

5.3.1 Calibrator Function of the CAD-IgM-IgA-IgG Modubody

Figure 12:
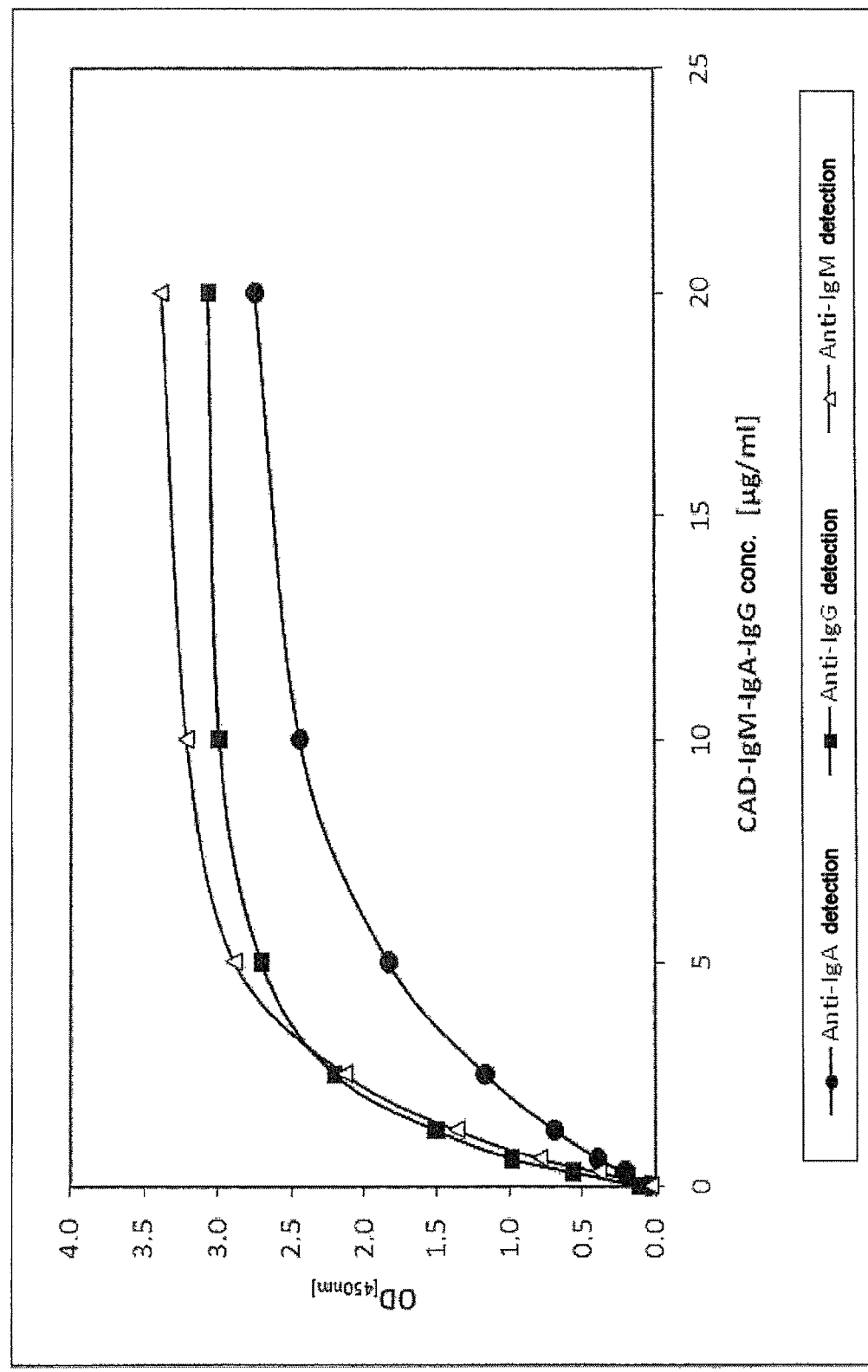

In order to determine whether the CAD-IgM-IgA-IgG modubody has retained the β2-glycoprotein-binding activity of the scFv-CAD and binding to the antigen can be detected via different isotype-specific antihuman secondary antibodies, purified CAD-IgM-IgA-IgG preparations were investigated in an anti-β2-glycoprotein/cardiolipin immunoassay. The purified CAD-IgM-IgA-IgG modubody was applied in a dilution series with concentrations of 0 µg/ml, 0.31 µg/ml, 0.62 µg/ml, 1.25 µg/ml, 2.5 µg/ml, 5 µg/ml, 10 µg/ml, 20 µg/ml in calibrator dilution medium to microtitre plates coated with β2-glycoprotein in complex with cardiolipin. The antigen-binding activity was determined under the incubation conditions provided for the anti-cardiolipin assay (ORG 515, ORGENTEC GmbH, Mainz) in separate determinations using antihuman IgM, antihuman IgA and antihuman IgG peroxidase-labelled secondary antibodies in concentrations of 80 ng/ml. FIG. 12 shows the variation in the OD 450 nm determinations with the chosen detection antibodies in dependence on the concentration of the CAD-IgM-IgA-IgG modubody. Under the chosen reaction conditions, the CAD-IgM-IgA-IgG modubody was detected at a concentration of 5 µg/ml on detection with antihuman IgM, antihuman IgA and antihuman IgG secondary antibodies with O.D. 450 nm values of 2.8, 1.8 and 2.7.

5.3.2 Stability of the CAD-IgM-IgA-IgG Modubody to Drying

Figure 13:
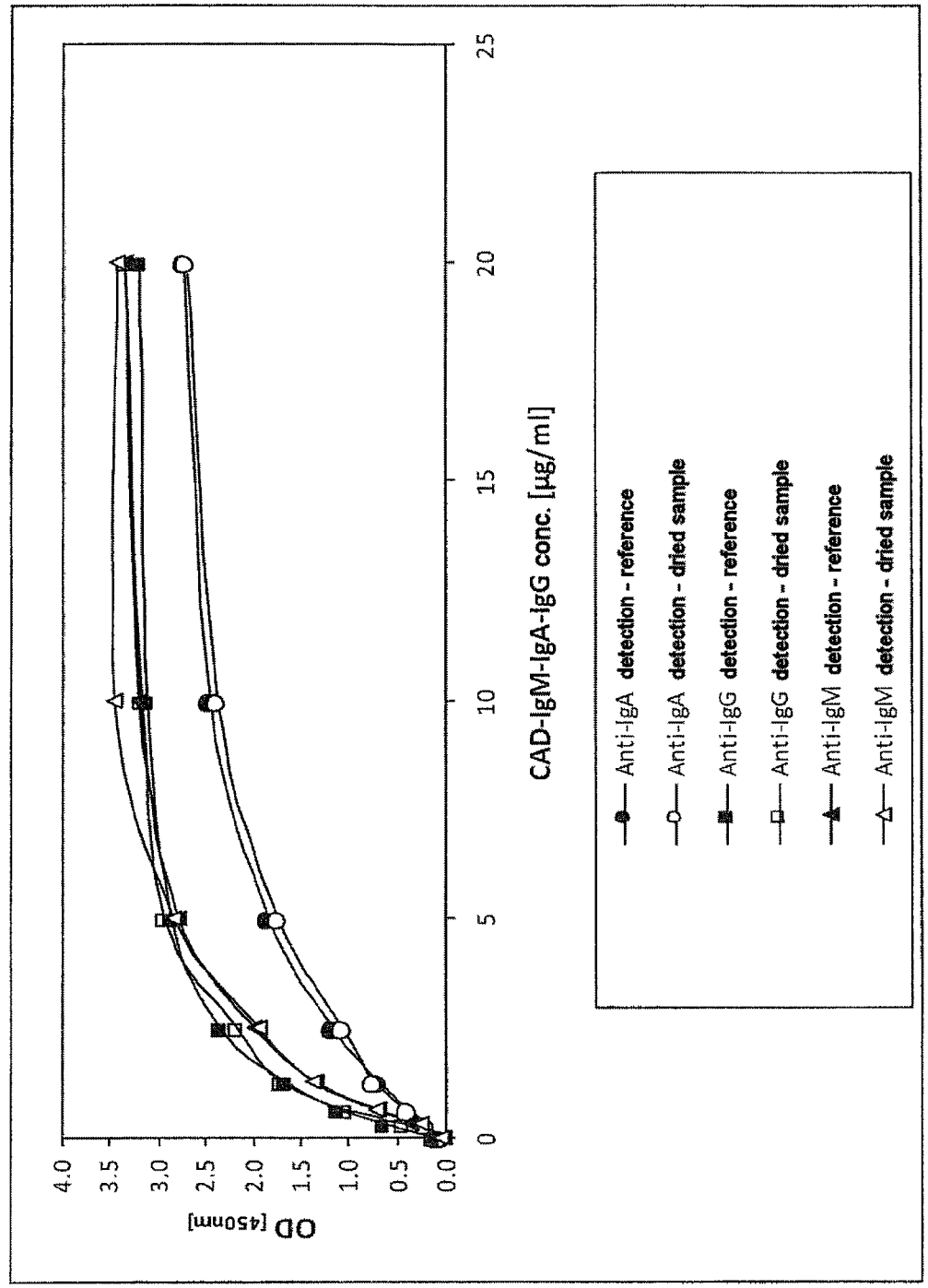

The stability to drying was investigated as follows: dilutions of the CAD-IgM-IgA-IgG modubody in calibrator dilution medium in 50 µl portions in concentrations of 0 µg/ml, 3.1 µg/ml, 6.21 µg/ml, 12.5 µg/ml, 25 µg/ml, 50 µg/ml, 100 µg/ml, 200 µg/ml were dried in vacuo at 22° C. in a Speedvak device. The dried samples were resolubilised with 450 µl of calibrator dilution medium and 50 µl of water to give a dilution series with concentrations of 0 µg/ml, 0.31 µg/ml, 0.62 µg/ml, 1.25 µg/ml, 2.5 µg/ml, 5 µg/ml, 10 µg/ml, 20 µg/ml and in comparison with an untreated dilution series were applied to microtitre plates coated with β2-glycoprotein in complex with cardiolipin. The antigen-binding activity was determined under the incubation conditions provided for the anti-cardiolipin assay (ORG 515, ORGENTEC GmbH, Mainz) in separate determinations using antihuman IgM, antihuman IgA and antihuman IgG peroxidase-labelled secondary antibodies (Jackson Immunoresearch) in concentrations of 80 ng/ml. FIG. 13 shows the variation in the OD 450 nm determinations with the chosen detection antibodies in untreated sample dilution steps in comparison with dried sample dilution steps. Under the chosen reaction conditions, the function of the CAD-IgM-IgA-IgG modubody in dilutions in the concentration range from 3.1 µg/ml to 200 µg/ml was not impaired by drying.

5.3.2.3 Stability of the CAD-IgM-IgA-IgG Modubody to Freeze-thaw Cycles

Figure 14:
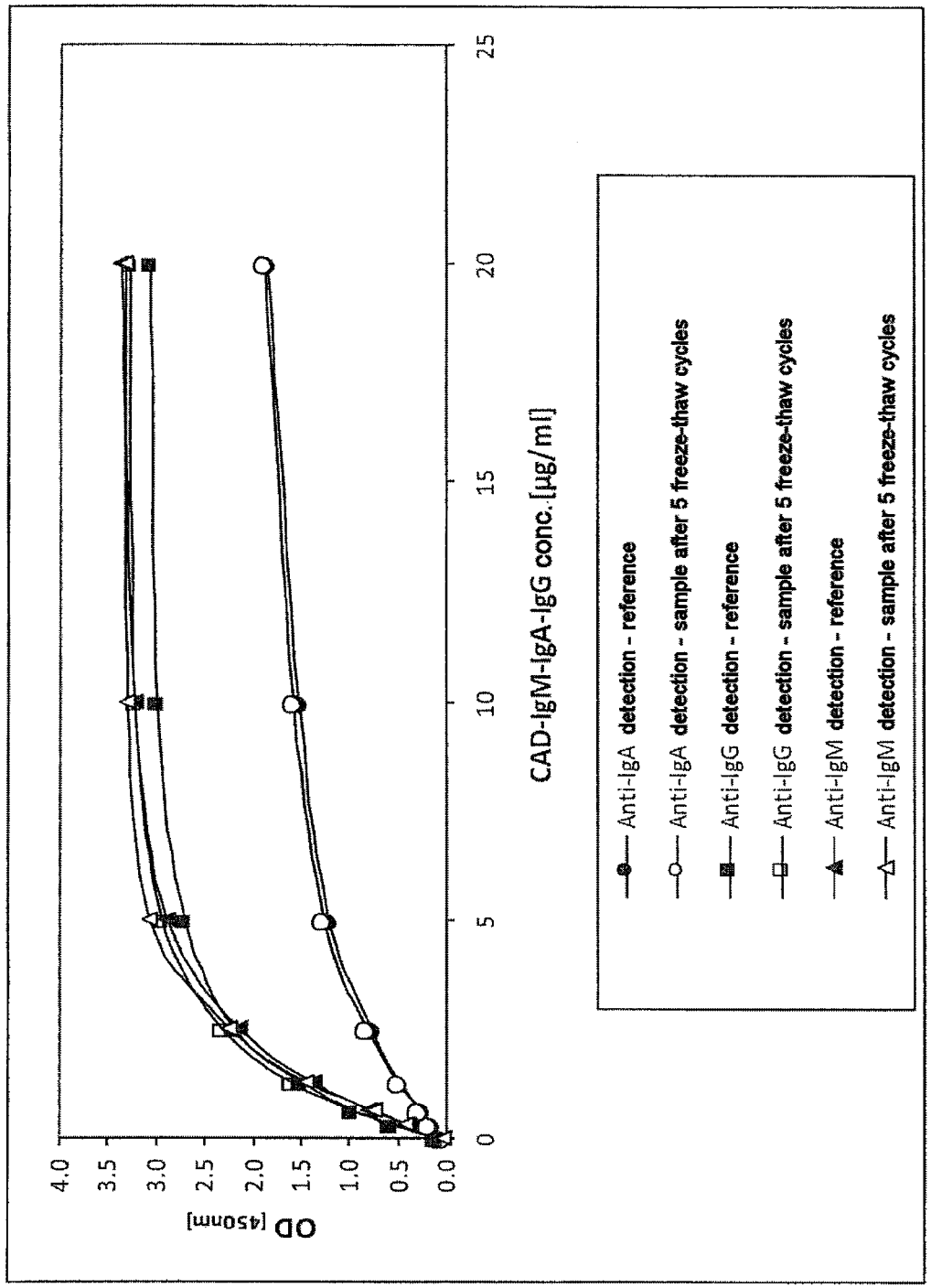

The stability to repeated freeze-thaw cycles was investigated as follows: dilutions of the CAD-IgM-IgA-IgG modubody in calibrator dilution medium in 50 µl portions in concentrations of 0 µg/ml, 6.21 µg/ml, 12.5 µg/ml, 25 µg/ml, 50 µg/ml, 100 µg/ml, 200 µg/ml were frozen at −70° C. and thawed again at 37° C. in five repeated freeze-thaw cycles. The samples were then diluted with 450 µl of calibrator dilution medium to give a dilution series with concentrations of 0 µg/ml, 0.31 µg/ml, 0.62 µg/ml, 1.25 µg/ml, 2.5 µg/ml, 5 µg/ml, 10 µg/ml, 20 µg/ml and in comparison with an untreated CAD-IgM-IgA-IgG dilution series were applied to microtitre plates coated with β2-glycoprotein in complex with cardiolipin. The antigen-binding activity was determined under the incubation conditions provided for the anti-cardiolipin assay (ORG 515, ORGENTEC GmbH, Mainz) in separate determinations using antihuman IgM, antihuman IgA and antihuman IgG peroxidase-labelled secondary antibodies (Jackson Immunoresearch) in concentrations of 80 ng/ml. FIG. 14 shows the variation in the OD 450 nm determinations with the chosen detection antibodies in the case of untreated sample dilution steps in comparison with the repeatedly frozen and thawed samples. Under the chosen reaction conditions, the function of the CAD-IgM-IgA-IgG modubody in dilutions in the concentration range from 3.1 µg/ml to 200 µg/ml was not impaired by repeated freeze-thaw cycles.

Example 6

The Single-chain CAD-IgG-CH3-Knob02 Modubody 6.1 Construction and Cloning of the Single-chain CAD-IgG-CH3-Knob02 Modubody The following example describes the construction and cloning of the β2-glycoprotein-specific modubody CAD-IgG-CH3-Knob02 provided with a monomeric modified human IgG-CH3-Knob02 detection domain For the construction of the CAD-IgG-CH3-Knob02 modubody, the modules scFv-CAD (Example 1) and IgG-CH3-Knob02 (Example 2.9) were assembled by restriction digestion and ligation in the domain sequence VL-linker-VH-linker-IgG-CH3-Knob02 to form a CAD-IgG-CH3-Knob02 coding sequence (SEQ ID NO: 34). To that end, the synthetic IgG-CH3-Knob02 reaction module Sc-RP-CH3-Knob02-G-N corresponding to sequence SEQ ID NO: 33 and described under Example 2.9 was freed from the vector construct IgG-CH3-Knob02-pMA by digestion with the restriction enzymes BamHI and HindIII.

The 417 by restriction fragment was gel-isolated after agarose gel electrophoresis with the QiaExII kit (Qiagen, Hilden) and ligated with the CAD-scFv-pQE80 vector construct described under Example 1, which was digested with the compatible enzymes BamHI and HindIII. The ligation products were transformed into E. coli strain NovaBlue (Merck, Nottingham). The transformation batch was plated out on LB agar plates supplemented with carbenicillin (50 µg/ml) and incubated overnight at 36° C. Single colonies of the resulting E. coli strain CAD-IgG-CH3-Knob02-pQE80-NovaBlue were propagated (36° C., overnight, 180 rpm) in LB medium supplemented with carbenicillin (50 µg/ml) (LB-Garb.). Stock cultures for freezing were prepared from the single clone cultures, in each case 1 ml of the single clone cultures was used for plasmid preparation. The isolated plasmids were analysed by EcoRI/HindIII digestion. Clones with an expected 1308 by fragment were investigated further by induction analysis. To that end, the chosen single clones were grown in LB-Carb. and, at an O.D. 500 of from 0.5 to 1.0, induced to expression of the protein coded for by the cloned DNA fragment by addition of one culture volume of LB-Carb. supplemented with 1 mM IPTG, and cultivated for 16 hours at 36° C., 180 rpm. The induction cells were lysed in SDS sample buffer, proteins were separated by SDS-PAGE. In the Western blot, the expression of the expected 44 kDa CAD-IgG-CH3-Knob02 modubody was detected by detection with an anti-RGS-6xHis peroxidase-coupled antibody (Qiagen, Hilden). The correct cloning was confirmed by sequencing.

6.2 Expression and Purification of the Single-chain CAD-IgG-CH3-Knob02 Modubody

The following example describes the expression and purification of the β2-glycoprotein-specific modubody CAD-IgG-CH3-Knob02 provided with a modified human IgG-CH3-Knob02 detection domain.

*E. coli* strain CAD-IgG-CH3-Knob02-pQE80-NovaBlue transformed under 6.1 with the expression construct was grown in LB-Carb. medium at 36° C. to an O.D. 500 of from 0.5 to 1.0 and induced to synthesis of the CAD-IgG-CH3-Knob02 modubody by addition of IPTG. The induced culture was cultivated at 36° C. for 4 hours to overnight. The induction cells were harvested and lysed after lysozyme treatment in an 8M urea-containing TBS buffer. Expressed CAD-IgG-CH3-Knob02 modubodies were purified by Ni-NTA affinity chromatography. A 44 kDa band is visible in the Coomassie blue-stained SDS-polyacrylamide gel. The enhancement of the β2-glycoprotein-binding activity and a reactivity with a peroxidase-coupled antihuman IgG secondary antibody (Jackson Immunoresearch) is associated with the purification of the 44 kDa band.

6.3 Binding of the CAD-IgG-CH3-Knob02 Modubody to β2-glycoprotein

Figure 15:
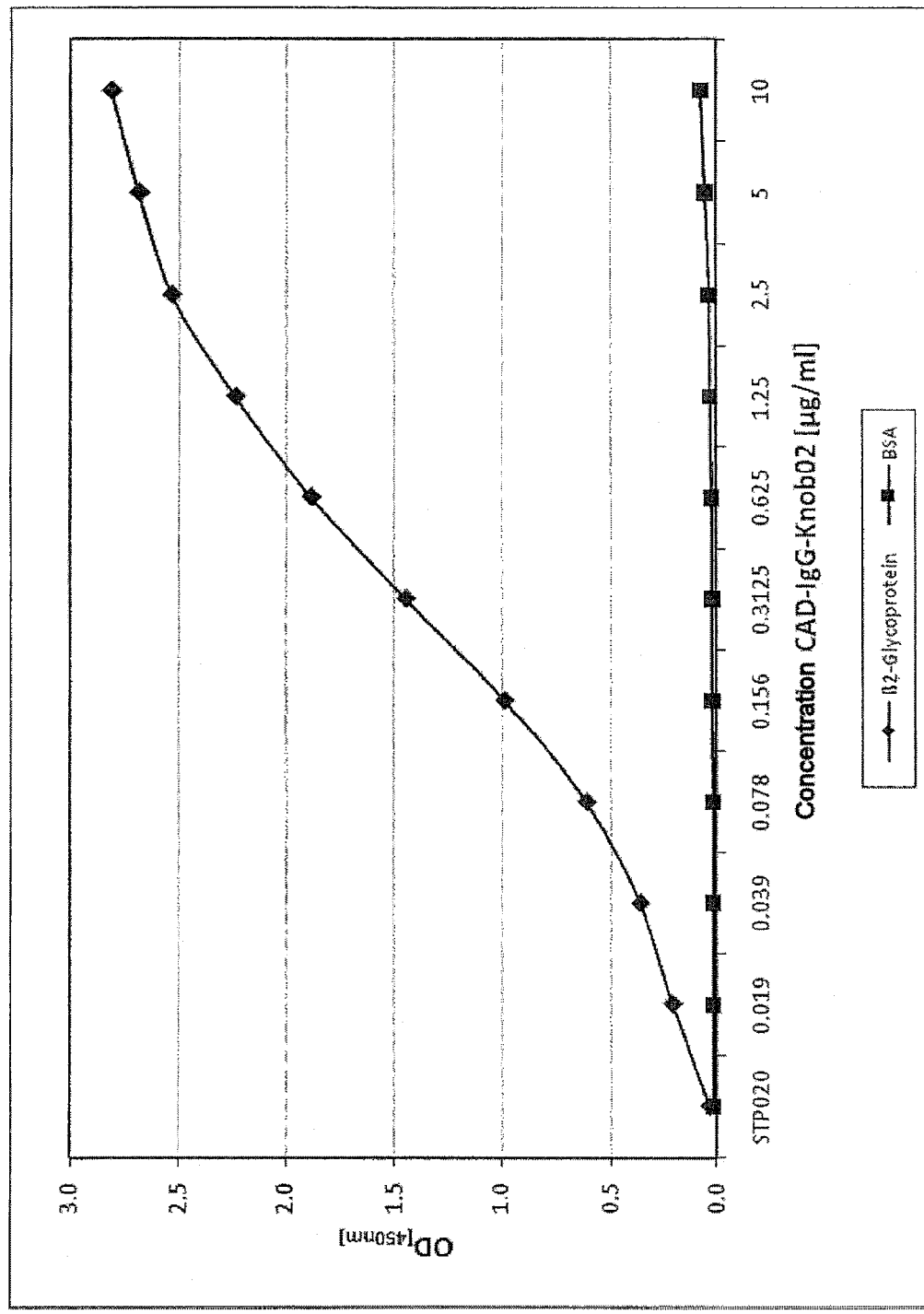

In order to determine whether the CAD-IgG-CH3-Knob02 modubody has retained the β2-glycoprotein-binding activity of the scFv-CAD, purified CAD-IgG-CH3-Knob02 preparations were tested by immunoassays. To that end, dilution series of the CAD-IgG-CH3-Knob02 modubody were applied to microtitre plates of the anti-β2-glycoprotein assay coated with β2-glycoprotein (ORG 521, ORGENTEC Diagnostika GmbH, Mainz) and, for control of the binding specificity, to BSA-coated plates, and incubated for 30 minutes at 20-25° C. The microtitre plates were washed and the binding of the CAD-IgG-CH3-Knob02 modubody was determined using a peroxidase-labelled RGS-6X-His antibody (Qiagen, Hilden) and a tetramethylbenzidine (TMB) colour reaction by measurement of the O.D. 450 nm. FIG. 15 shows the variation in the OD 450 nm determined under the chosen reaction conditions in dependence on the concentration. Specific binding to β2-glycoprotein was detected even at a concentration of the CAD-IgG-CH3-Knob02 modubody of 19 ng/ml. Comparison of the level of reaction of the CAD-IgG-CH3-Knob32 dilution steps in the case of binding to β2-glycoprotein- or BSA-coated microtitre plates shows that no non-specific binding occurs in the concentration range of 0.019-10 μg/ml CAD-IgG-CH3-Knob02.

The invention claimed is:

1. Monovalent fusion polypeptide which is present in the form of a monomer under non-denaturing conditions, comprising
   (i) a first domain comprising the heavy chain variable region of an antibody (VH) or at least a section thereof that mediates antigen binding,
   (ii) a second domain comprising the light chain variable region of an antibody (VL) or at least a section thereof that mediates antigen binding, and
   (iii) a third domain comprising a section of a heavy chain constant region of an antibody (CHX),
   wherein domain (iii) has a length of from 80 to 130 amino acid residues,
   wherein domains (i), (ii) and (iii) are linked together via peptide linkers (L),
   wherein the peptide linkers (L) each independently have a length of from 25 to 45 amino acid residues and consist of sequences which are heterologous to the amino acid sequences of the first, second and third domains, wherein the monovalent fusion polypeptide has antigen binding activity and over 90% of said antigen binding activity remains after 10 days incubation at 36° C. or after drying and reconstitution or after freeze/thaw cycles repeated 5 times and wherein the monovalent fusion polypeptide does not form intermolecular disulphide bridges and is free of hinge regions of antibodies.

2. Fusion polypeptide according to claim 1, comprising the structure

VH-L-VL-L-CHX or

VL-L-VH-L-CHX.

3. Fusion polypeptide according to claim 1, wherein domains (i), (ii) and (iii) each have a length of from 80 to 130 amino acid residues.

4. Fusion polypeptide according to claim 1, wherein domain (iii) is selected from sections CH1, CH2, CH3 and CH4 of antibodies, or combinations of these sections.

5. Fusion polypeptide according to claim 1, wherein the peptide linkers each independently have a length of from 30 to 40 amino acid residues.

6. Fusion polypeptide according to claim 1, wherein the peptide linkers consist of at least 90% glycine and/or serine residues.

7. Fusion polypeptide according to claim 1, which has at least one additional domain, for example a signal peptide and/or a peptide tag.

8. Fusion polypeptide according to claim 1, which has one or more domains VH, VL and/or CHX selected from the group consisting of SEQ ID NO: 1 (VL), SEQ ID NO: 2 (VH), SEQ ID NO: 4 (VH, VL), SEQ ID NO: 8 (IgG-CH1), SEQ ID NO: 10 (IgG-CH2), SEQ ID NO: 12 (IgG-CH3), SEQ ID NO: 14 (IgA-CH2), SEQ ID NO: 16 (IgA-CH3), SEQ ID NO: 18 (IgM-CH2), SEQ ID NO: 20 (IgM-CH3) or SEQ ID NO: 22 (IgM-CH4).

9. Fusion polypeptide according to claim 1, wherein at least one asparagine residue from a glycosylation position is replaced by a different amino acid residue.

10. Fusion polypeptide according to claim 1, wherein at least one cysteine residue in domain (iii) is replaced by serine, alanine or glycine.

11. Fusion polypeptide according to claim 1 for use in medicine, for example in human or veterinary medicine.

12. Pharmaceutical composition comprising a fusion polypeptide according to claim 1, together with pharmaceutically suitable carrier substances.

13. The fusion polypeptide according to claim 4, wherein said antibodies, are selected from the group consisting of classes IgG, IgM, IgE and IgA.

14. The fusion polypeptide according to claim 4, wherein said antibodies, are human or mouse antibodies.

15. The fusion polypeptide according to claim 8, which has one or more domains VH, VL and/or CHX which have at least 95% identity, at amino acid level with the corresponding domains according to SEQ ID NO: 1 (VL), SEQ ID NO: 2 (VH), SEQ ID NO: 4 (VH, VL), SEQ ID NO: 8 (IgG-CH1), SEQ ID NO: 10 (IgG-CH2), SEQ ID NO: 12 (IgG-CH3), SEQ ID NO: 14 (IgA-CH2), SEQ ID NO: 16 (IgA-CH3), SEQ ID NO: 18 (IgM-CH2), SEQ ID NO: 20 (IgM-CH3) or SEQ ID NO: 22 (IgM-CH4).

16. The fusion polypeptide according to claim 9, wherein said different amino acid residue is serine, alanine or glycine.

17. The fusion polypeptide according to claim 10, wherein said different amino acid residue is serine, alanine or glycine.

18. Monovalent fusion polypeptide which is present in the form of a monomer under non-denaturing conditions, comprising
   (i) a first domain comprising the heavy chain variable region of an antibody (VH) or at least a section thereof that mediates antigen binding,
   (ii) a second domain comprising the light chain variable region of an antibody (VL) or at least a section thereof that mediates antigen binding, and
   (iii) a third domain comprising a section of a heavy chain constant region of an antibody (CHX),
   wherein domain (iii) has a length of from 80 to 130 amino acid residues,
   wherein domains (i), (ii) and (iii) are linked together via peptide linkers (L),
   wherein the peptide linkers (L) each independently have a length of from 25 to 45 amino acid residues, consist of sequences which are heterologous to the amino acid sequences of the first, second and third domains and contain a plurality of sequences SGGGG, wherein the monovalent fusion polypeptide has antigen binding activity and over 90% of said antigen binding activity remains after 10 days incubation at 36° C. or after drying and reconstitution or after freeze/thaw cycles repeated 5 times and wherein the monovalent fusion polypeptide does not form intermolecular disulphide bridges and is free of hinge regions of antibodies.

19. The monovalent fusion polypeptide according to claim 18, wherein the peptide linkers (L) comprise three GGGGS and three SGGGG blocks.

* * * * *

SEQUENCE LISTING

```
<160> NUMBER OF SEQ ID NOS: 34

<210> SEQ ID NO 1
<211> LENGTH: 112
<212> TYPE: PRT
<213> ORGANISM: Artificial
<220> FEATURE:
<223> OTHER INFORMATION: WBCAL-1 VL

<400> SEQUENCE: 1

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Tyr Thr Phe Gly Gly Gly Thr Lys Leu Glu Ile Lys
            100                 105                 110

<210> SEQ ID NO 2
<211> LENGTH: 114
<212> TYPE: PRT
<213> ORGANISM: Artificial
<220> FEATURE:
<223> OTHER INFORMATION: WBCAL-1 VH
```

-continued

```
<400> SEQUENCE: 2

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Tyr
            20                  25                  30

Tyr Met His Trp Val Arg Gln Arg Pro Gly Gln Gly Leu Glu Trp Ile
        35                  40                  45

Gly Glu Ile Tyr Pro Gly Ser Gly Asn Thr Ser Tyr Asn Glu Lys Phe
    50                  55                  60

Arg Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Gly Thr Leu Asp Tyr Thr Met Asp Tyr Trp Gly Gln Gly Thr
            100                 105                 110

Ser Val

<210> SEQ ID NO 3
<211> LENGTH: 36
<212> TYPE: PRT
<213> ORGANISM: Artificial
<220> FEATURE:
<223> OTHER INFORMATION: peptide linker

<400> SEQUENCE: 3

Gly Ser Gly Gly Gly Gly Ser Gly Gly Gly Gly Ser Gly Gly Gly Gly
1               5                   10                  15

Ser Ser Gly Gly Gly Gly Ser Gly Gly Gly Gly Ser Gly Gly Gly Gly
            20                  25                  30

Ser Gly Ser Gly
            35

<210> SEQ ID NO 4
<211> LENGTH: 276
<212> TYPE: PRT
<213> ORGANISM: Artificial
<220> FEATURE:
<223> OTHER INFORMATION: scFv-RP-CAD-P
<220> FEATURE:
<221> NAME/KEY: DOMAIN
<222> LOCATION: (1)..(118)
<223> OTHER INFORMATION: VL domain
<220> FEATURE:
<221> NAME/KEY: DOMAIN
<222> LOCATION: (159)..(272)
<223> OTHER INFORMATION: VH domain

<400> SEQUENCE: 4

Leu Val Pro Arg Gly Ser Asp Val Leu Met Thr Gln Thr Pro Leu Ser
1               5                   10                  15

Leu Pro Val Ser Leu Gly Asp Gln Ala Ser Ile Ser Cys Arg Ser Ser
            20                  25                  30

Gln Ser Ile Val His Ser Asn Gly Asn Thr Tyr Leu Glu Trp Tyr Leu
        35                  40                  45

Gln Lys Pro Gly Gln Ser Pro Lys Leu Leu Ile Tyr Lys Val Ser Asn
    50                  55                  60

Arg Phe Ser Gly Val Pro Asp Arg Phe Ser Gly Ser Gly Ser Gly Thr
65                  70                  75                  80

Asp Phe Thr Leu Lys Ile Ser Arg Val Glu Ala Glu Asp Leu Gly Val
                85                  90                  95
```

```
Tyr Tyr Cys Phe Gln Gly Ser His Val Pro Tyr Thr Phe Gly Gly Gly
            100                 105                 110

Thr Lys Leu Glu Ile Lys Arg Thr Gly Ser Gly Ser Gly Gly Gly Gly
        115                 120                 125

Ser Gly Gly Gly Gly Ser Gly Gly Gly Gly Ser Gly Gly Gly Gly Gly
    130                 135                 140

Ser Gly Gly Gly Ser Gly Gly Gly Gly Ser Gly Ser Gly Glu Val
145                 150                 155                 160

Gln Leu Gln Gln Ser Gly Pro Glu Leu Val Lys Pro Gly Ala Ser Val
                165                 170                 175

Lys Ile Ser Cys Lys Ala Ser Gly Tyr Thr Phe Thr Asp Tyr Tyr Met
            180                 185                 190

His Trp Val Arg Gln Arg Pro Gly Gln Gly Leu Glu Trp Ile Gly Glu
            195                 200                 205

Ile Tyr Pro Gly Ser Gly Asn Thr Ser Tyr Asn Glu Lys Phe Arg Gly
            210                 215                 220

Lys Ala Thr Leu Thr Ala Asp Lys Ser Ser Ser Thr Ala Tyr Met Gln
225                 230                 235                 240

Leu Ser Ser Leu Thr Ser Glu Asp Ser Ala Val Tyr Phe Cys Ala Arg
                245                 250                 255

Gly Thr Leu Asp Tyr Thr Met Asp Tyr Trp Gly Gln Gly Thr Ser Val
            260                 265                 270

Thr Val Ser Ser
        275

<210> SEQ ID NO 5
<211> LENGTH: 862
<212> TYPE: DNA
<213> ORGANISM: Artificial
<220> FEATURE:
<223> OTHER INFORMATION: scFv-RP-CAD-N

<400> SEQUENCE: 5
ggtaccggat ccctggttcc gcgtggttct gatgttctga tgacccagac accgctgtct    60
ctgccggtta gcctgggtga tcaggcaagc attagctgtc gtagcagcca gagcattgtt   120
catagcaatg gcaataccta tctggaatgg tatctgcaga aaccgggtca gagcccgaaa   180
ctgctgattt ataaagtgag caatcgcttt agcggtgttc cggatcgttt tagcggttca   240
ggttctggca ccgatttac cctgaaaatt agccgtgttg aagcagaaga tctgggcgtt   300
tattattgtt ttcagggtag ccatgttccg tatacctttg gtggtggcac caaactggaa   360
attaaacgta ccggtagcgg tagtggaggt ggtggaagcg gtggtggcgg ttctggcggt   420
ggaggttctt ctggtggcgg tggatcaggt ggaggtggct caggcggtgg cggtagcggc   480
agcggtgaag ttcagctgca gcagagcggt ccggaactgg ttaaaccggg tgcaagcgtt   540
aaaattagct gtaaagccag cggctatacc tttaccgatt attatatgca ttgggttcgt   600
cagcgtccgg gtcagggtct ggaatggatt ggtgaaattt atccgggtag cggtaatacc   660
agctataatg aaaaatttcg tggcaaagca accctgaccg cagataaaag cagcagcacc   720
gcatatatgc agctgtctag cctgaccagc gaagatagcg cagtttactt ttgtgcacgt   780
ggcaccctgg attataccat ggattattgg ggacagggca ccagcgttac cgttagcagc   840
ggatcctaat aagcttgagc tc                                             862

<210> SEQ ID NO 6
```

```
<211> LENGTH: 27
<212> TYPE: DNA
<213> ORGANISM: Artificial
<220> FEATURE:
<223> OTHER INFORMATION: primer RP-CAD01

<400> SEQUENCE: 6
agtagatctc tggttccgcg tggttct                                27

<210> SEQ ID NO 7
<211> LENGTH: 18
<212> TYPE: DNA
<213> ORGANISM: Artificial
<220> FEATURE:
<223> OTHER INFORMATION: primer RP-CAD02

<400> SEQUENCE: 7
ctcaagctta ttaggatc                                          18

<210> SEQ ID NO 8
<211> LENGTH: 131
<212> TYPE: PRT
<213> ORGANISM: Artificial
<220> FEATURE:
<223> OTHER INFORMATION: Sc-RP-CH1-G-P
<220> FEATURE:
<221> NAME/KEY: DOMAIN
<222> LOCATION: (37)..(131)
<223> OTHER INFORMATION: IgG-CH1 domain

<400> SEQUENCE: 8
```

Gly Ser Gly Gly Gly Gly Ser Gly Gly Gly Gly Ser Gly Gly Gly
1               5                   10                  15

Ser Ser Gly Gly Gly Gly Ser Gly Gly Gly Gly Ser Gly Gly Gly Gly
                20                  25                  30

Ser Gly Ser Gly Gly Pro Ser Val Phe Pro Leu Ala Pro Ser Ser Lys
            35                  40                  45

Ser Thr Ser Gly Gly Thr Ala Ala Leu Gly Cys Leu Val Lys Asp Tyr
    50                  55                  60

Phe Pro Glu Pro Val Thr Val Ser Trp Asn Ser Gly Ala Leu Thr Ser
65                  70                  75                  80

Gly Val His Thr Phe Pro Ala Val Leu Gln Ser Ser Gly Leu Tyr Ser
                85                  90                  95

Leu Ser Ser Val Val Thr Val Pro Ser Ser Ser Leu Gly Thr Gln Thr
            100                 105                 110

Tyr Ile Cys Asn Val Asn His Lys Pro Ser Asn Thr Lys Val Asp Lys
        115                 120                 125

Lys Val Glu
    130

```
<210> SEQ ID NO 9
<211> LENGTH: 427
<212> TYPE: DNA
<213> ORGANISM: Artificial
<220> FEATURE:
<223> OTHER INFORMATION: Sc-RP-CH1-G-N

<400> SEQUENCE: 9
gagctcggat ccggcagtgg tggaggtggc tcaggcggag gtggaagcgg tggaggcggt    60
tcttcaggtg gcggtggaag tggcggtgga ggtagtggtg gcggaggctc tggatcaggt   120
ggtccgagcg ttttccgct ggcaccgagc agcaaaagca ccagcggtgg cacagcagca    180
```

```
ctgggctgtc tggtgaaaga ttatttccg gaaccggtta ccgttagctg gaatagcggt        240
gcactgacca gcggtgttca tacctttccg gcagttctgc agagcagcgg tctgtatagc        300
ctgagcagcg ttgttaccgt tccgtctagc agcctgggca cccagaccta tatttgcaat        360
gtgaatcata aaccgagcaa tacgaaagtg gataaaaaag tggaaggatc ctgataagct        420
tggtacc                                                                  427

<210> SEQ ID NO 10
<211> LENGTH: 138
<212> TYPE: PRT
<213> ORGANISM: Artificial
<220> FEATURE:
<223> OTHER INFORMATION: Sc-RP-CH2-G-P
<220> FEATURE:
<221> NAME/KEY: DOMAIN
<222> LOCATION: (37)..(138)
<223> OTHER INFORMATION: IgG-CH2 domain

<400> SEQUENCE: 10

Gly Ser Gly Gly Gly Ser Gly Gly Gly Ser Gly Gly Gly Gly
 1               5                  10                  15

Ser Ser Gly Gly Gly Gly Ser Gly Gly Gly Ser Gly Gly Gly Gly
            20                  25                  30

Ser Gly Ser Gly Gly Pro Asp Val Phe Leu Phe Pro Pro Lys Pro Lys
         35                  40                  45

Asp Thr Leu Met Ile Ser Arg Thr Pro Glu Val Thr Cys Val Val Val
 50                  55                  60

Asp Val Ser His Glu Asp Pro Glu Val Lys Phe Asn Trp Tyr Val Asp
65                  70                  75                  80

Gly Val Glu Val His Asn Ala Lys Thr Lys Pro Arg Glu Glu Gln Tyr
                85                  90                  95

Asn Ser Thr Tyr Arg Val Val Ser Val Leu Thr Val Leu His Gln Asp
            100                 105                 110

Trp Leu Asn Gly Lys Glu Tyr Lys Cys Lys Val Ser Asn Lys Ala Leu
        115                 120                 125

Pro Leu Pro Glu Glu Lys Thr Ile Ser Lys
    130                 135

<210> SEQ ID NO 11
<211> LENGTH: 448
<212> TYPE: DNA
<213> ORGANISM: Artificial
<220> FEATURE:
<223> OTHER INFORMATION: Sc-RP-CH2-G-N

<400> SEQUENCE: 11
gagctcggat ccggttctgg tggggagggg tctggcggag gtggctctgg cggaggcggt         60
tcaagcggtg gcggaggtag tggcggtggt ggtagtggag gcggaggctc tggttcaggt        120
ggtccggatg ttttttctgtt ccgcctaaa ccgaaagata ccctgatgat tagccgtaca        180
ccggaagtta cctgtgttgt tgttgatgtg agccatgaag atccggaagt gaaatttaat        240
tggtatgtgg atggtgtgga agttcataat gccaaaacca aaccgcgtga agaacagtat        300
aatagcacct atcgtgttgt ttctgttctg accgttctgc atcaggattg gctgaatggc        360
aaagaatata atgcaaagt gtctaataaa gcactgccgc tgccggaaga aaaaaccatt        420
agcaaaggat cctaataagc ttggtacc                                           448

<210> SEQ ID NO 12
```

<211> LENGTH: 135
<212> TYPE: PRT
<213> ORGANISM: Artificial
<220> FEATURE:
<223> OTHER INFORMATION: Sc-RP-CH3-G-P
<220> FEATURE:
<221> NAME/KEY: DOMAIN
<222> LOCATION: (37)..(135)
<223> OTHER INFORMATION: IgG-CH3 domain

<400> SEQUENCE: 12

```
Gly Ser Gly Gly Gly Ser Gly Gly Gly Ser Gly Gly Gly Gly
  1               5                  10                  15
Ser Ser Gly Gly Gly Gly Ser Gly Gly Gly Ser Gly Gly Gly Gly
             20                  25                  30
Ser Gly Ser Gly Glu Pro Gln Val Tyr Thr Leu Pro Pro Ser Arg Glu
         35                  40                  45
Glu Met Thr Lys Asn Gln Val Ser Leu Thr Cys Leu Val Lys Gly Phe
     50                  55                  60
Tyr Pro Ser Asp Ile Ala Val Glu Trp Glu Ser Asn Gly Gln Pro Glu
 65                  70                  75                  80
Asn Asn Tyr Lys Thr Thr Pro Pro Val Leu Asp Ser Asp Gly Ser Phe
                 85                  90                  95
Phe Leu Tyr Ser Lys Leu Thr Val Asp Lys Ser Arg Trp Gln Gln Gly
            100                 105                 110
Asn Val Phe Ser Cys Ser Val Met His Glu Ala Leu His Asn His Tyr
        115                 120                 125
Thr Gln Lys Ser Leu Ser Leu
    130                 135
```

<210> SEQ ID NO 13
<211> LENGTH: 439
<212> TYPE: DNA
<213> ORGANISM: Artificial
<220> FEATURE:
<223> OTHER INFORMATION: Sc-RP-CH3-G-N

<400> SEQUENCE: 13

```
gagctcggat ccggtagcgg tggtggtggt tctggcggtg gtggcagcgg aggtggcggt    60
agctcaggtg gcggaggtag tggcggtgga ggcagtggtg gcggtggctc tggatctggt   120
gaaccgcagg tttatacccct gcctccgagc cgtgaagaaa tgaccaaaaa tcaggttagc   180
ctgacctgtc tggtgaaagg ttttatccg agcgatattg cagttgaatg gaaagcaat    240
ggtcagccgg aaaataatta taaaaccaca cctccggttc tggattctga tggtagcttt   300
tttctgtata gcaaactgac cgttgataaa agccgttggc agcagggtaa tgttttttagc   360
tgtagcgtta tgcatgaagc cctgcataat cattataccc agaaaagcct gagcctggga   420
tcctaataag cttggtacc                                                439
```

<210> SEQ ID NO 14
<211> LENGTH: 133
<212> TYPE: PRT
<213> ORGANISM: Artificial
<220> FEATURE:
<223> OTHER INFORMATION: Sc-RP-CH2-A-P
<220> FEATURE:
<221> NAME/KEY: DOMAIN
<222> LOCATION: (37)..(133)
<223> OTHER INFORMATION: IgA-CH2 domain

<400> SEQUENCE: 14

```
Gly Ser Gly Gly Gly Gly Ser Gly Gly Gly Ser Gly Gly Gly
1               5                   10                  15

Ser Ser Gly Gly Gly Gly Ser Gly Gly Gly Ser Gly Gly Gly
            20                  25                  30

Ser Gly Ser Gly Arg Leu Ser Leu His Arg Pro Ala Leu Glu Asp Leu
        35                  40                  45

Leu Leu Gly Ser Glu Ala Asn Leu Thr Cys Thr Leu Thr Gly Leu Arg
    50                  55                  60

Asp Ala Ser Gly Val Thr Phe Thr Trp Thr Pro Ser Ser Gly Lys Ser
65                  70                  75                  80

Ala Val Gln Gly Pro Pro Glu Arg Asp Leu Cys Gly Ser Tyr Ser Val
            85                  90                  95

Ser Ser Val Leu Pro Gly Ser Ala Glu Pro Trp Asn His Gly Lys Thr
        100                 105                 110

Phe Thr Cys Thr Ala Ala Tyr Pro Glu Ser Lys Thr Pro Leu Thr Ala
        115                 120                 125

Thr Leu Ser Lys Ser
    130
```

<210> SEQ ID NO 15
<211> LENGTH: 433
<212> TYPE: DNA
<213> ORGANISM: Artificial
<220> FEATURE:
<223> OTHER INFORMATION: Sc-RP-CH2-A-N

<400> SEQUENCE: 15

```
gagctcggat ccggaagtgg cggaggcgga tcaggtggag gtggcagcgg aggtggcggt      60
agctctggtg gcgtggtag tggcggtgga ggtagtggtg gcggaggctc tggttctggt     120
cgtctgagcc tgcatcgtcc ggcactggaa gatctgctgc tgggtagcga agcaaatctg     180
acctgtaccc tgaccggtct gcgtgatgca agcggtgtta catttacctg gaccccgagc     240
agcggtaaaa gcgcagttca gggtccgcct gaacgtgatc tgtgtggtag ctatagcgtt     300
agcagcgttc tgcctggtag cgcagaaccg tggaatcatg gtaaaacctt acctgtacc     360
gcagcatatc cggaaagcaa aacaccgctg accgcaaccc tgagcaaaag cggatcctaa     420
taagcttggt acc                                                        433
```

<210> SEQ ID NO 16
<211> LENGTH: 141
<212> TYPE: PRT
<213> ORGANISM: Artificial
<220> FEATURE:
<223> OTHER INFORMATION: sc-RP-CH3-A-P
<220> FEATURE:
<221> NAME/KEY: DOMAIN
<222> LOCATION: (37)..(141)
<223> OTHER INFORMATION: IgA-CH3 domain

<400> SEQUENCE: 16

```
Gly Ser Gly Gly Gly Gly Ser Gly Gly Gly Ser Gly Gly Gly
1               5                   10                  15

Ser Ser Gly Gly Gly Gly Ser Gly Gly Gly Ser Gly Gly Gly
            20                  25                  30

Ser Gly Ser Gly Arg Pro Glu Val His Leu Leu Pro Pro Ser Glu
        35                  40                  45

Glu Leu Ala Leu Asn Glu Leu Val Thr Leu Thr Cys Leu Ala Arg Gly
    50                  55                  60
```

Phe Ser Pro Lys Asp Val Leu Val Arg Trp Leu Gln Gly Ser Gln Glu
65                  70                  75                  80

Leu Pro Arg Glu Lys Tyr Leu Thr Trp Ala Ser Arg Gln Glu Pro Ser
                85                  90                  95

Gln Gly Thr Thr Thr Phe Ala Val Thr Ser Ile Leu Arg Val Ala Ala
            100                 105                 110

Glu Asp Trp Lys Lys Gly Asp Thr Phe Ser Cys Met Val Gly His Glu
        115                 120                 125

Ala Leu Pro Leu Ala Phe Thr Gln Lys Thr Ile Asp Arg
    130                 135                 140

<210> SEQ ID NO 17
<211> LENGTH: 457
<212> TYPE: DNA
<213> ORGANISM: Artificial
<220> FEATURE:
<223> OTHER INFORMATION: sc-RP-CH3-A-N

<400> SEQUENCE: 17
gagctcggat ccggtagcgg aggtggcgga agcggaggtg gaggcagtgg tggaggcggt      60
agctcaggtg gcggtggaag tggtggaggt ggctcagggg gtggaggttc tggttctggt     120
cgtccggaag ttcatctgct gcctccgcct agcgaagaac tggcactgaa tgaactggtt     180
accctgacct gtctggcacg tggttttagc ccgaaagatg ttctggttcg ttggctgcag     240
ggtagccagg aactgcctcg cgaaaaatat ctgacctggg catctcgcca ggaaccgagc     300
cagggcacca ccacctttgc agttaccagc attctgcgtg ttgcagcaga agattggaaa     360
aaaggcgata ccttagctg tatggttggt catgaagcac tgccgctggc atttacccag     420
aaaaccatcg atcgcggatc ctaataagct tggtacc                              457

<210> SEQ ID NO 18
<211> LENGTH: 148
<212> TYPE: PRT
<213> ORGANISM: Artificial
<220> FEATURE:
<223> OTHER INFORMATION: Sc-RP-CH2-M-P
<220> FEATURE:
<221> NAME/KEY: DOMAIN
<222> LOCATION: (37)..(148)
<223> OTHER INFORMATION: IgM-CH2 domain

<400> SEQUENCE: 18

Gly Ser Gly Gly Gly Gly Ser Gly Gly Gly Gly Ser Gly Gly Gly Gly
1               5                   10                  15

Ser Ser Gly Gly Gly Gly Ser Gly Gly Gly Ser Gly Gly Gly Gly
                20                  25                  30

Ser Gly Ser Gly Ile Ala Glu Leu Pro Pro Lys Val Ser Val Phe Val
            35                  40                  45

Pro Pro Arg Asp Gly Phe Phe Gly Asn Pro Arg Lys Ser Lys Leu Ile
        50                  55                  60

Cys Gln Ala Thr Gly Phe Ser Pro Arg Gln Ile Gln Val Ser Trp Leu
65                  70                  75                  80

Arg Glu Gly Lys Gln Val Gly Ser Gly Val Thr Thr Asp Gln Val Gln
                85                  90                  95

Ala Glu Ala Lys Glu Ser Gly Pro Thr Thr Tyr Lys Val Thr Ser Thr
            100                 105                 110

Leu Thr Ile Lys Glu Ser Asp Trp Leu Gly Gln Ser Met Phe Thr Cys
        115                 120                 125

Arg Val Asp His Arg Gly Leu Thr Phe Gln Gln Ser Ala Ser Ser Met
130                 135                 140

Ser Val Pro Asp
145

<210> SEQ ID NO 19
<211> LENGTH: 478
<212> TYPE: DNA
<213> ORGANISM: Artificial
<220> FEATURE:
<223> OTHER INFORMATION: Sc-RP-CH2-M-N

<400> SEQUENCE: 19
gagctcggat ccggttcagg tggtggtggt tctggtggtg aggcagtggg aggtggcggt      60
tctagcggtg gcggtggaag tggcggaggt ggcagtggtg gcggtggctc tggttctggt     120
attgcagaac tgcctccgaa agttagcgtt tttgttcctc cgcgtgatgg ttttttttggt    180 aatccgcgta aaagcaaact gatttgtcag gcaaccggtt tttctccgcg tcagattcag     240
gttagctggc tgcgtgaagg taaacaggtt ggtagcggtt taccaccgat caggttcag      300 gcagaagcaa agaaagcgg tccgaccacc tataaagtta ccagcaccct gaccattaaa     360
gaaagcgatt ggctgggtca gagcatgttt acctgtcgtg ttgatcatcg tggtctgacc     420
tttcagcaga gcgcaagcag catgagcgtt ccggatggat cctaataagc ttggtacc      478

<210> SEQ ID NO 20
<211> LENGTH: 142
<212> TYPE: PRT
<213> ORGANISM: Artificial
<220> FEATURE:
<223> OTHER INFORMATION: Sc-RP-CH3-M-P
<220> FEATURE:
<221> NAME/KEY: DOMAIN
<222> LOCATION: (37)..(142)
<223> OTHER INFORMATION: IgM-CH3 domain

<400> SEQUENCE: 20

Gly Ser Gly Gly Gly Gly Ser Gly Gly Gly Gly Ser Gly Gly Gly Gly
1               5                   10                  15

Ser Ser Gly Gly Gly Gly Ser Gly Gly Gly Ser Gly Gly Gly Gly
                20                  25                  30

Ser Gly Ser Gly Gln Asp Thr Ala Ile Arg Val Phe Ala Ile Pro Pro
            35                  40                  45

Ser Phe Ala Ser Ile Phe Leu Thr Lys Ser Thr Lys Leu Thr Cys Leu
    50                  55                  60

Val Thr Asp Leu Thr Thr Tyr Asp Ser Val Thr Ile Ser Trp Thr Arg
65                  70                  75                  80

Gln Asn Gly Glu Ala Val Lys Thr His Thr Ser Ile Ser Glu Ser His
                85                  90                  95

Pro Ser Ala Thr Phe Ser Ala Val Gly Glu Ala Ser Ile Ser Glu Asp
            100                 105                 110

Asp Trp Asn Ser Gly Glu Arg Phe Thr Cys Thr Val Thr His Thr Asp
        115                 120                 125

Leu Pro Ser Pro Leu Lys Gln Thr Ile Ser Arg Pro Lys Gly
    130                 135                 140

<210> SEQ ID NO 21
<211> LENGTH: 460
<212> TYPE: DNA
<213> ORGANISM: Artificial
<220> FEATURE:

<223> OTHER INFORMATION: Sc-RP-CH3-M-N

<400> SEQUENCE: 21

```
gagctcggat ccggaagtgg tggaggtggc agcggtggtg gtggctctgg tggaggcggt      60
agctcaggtg gcggtggtag tggcggtgga ggtagtggtg gcggaggttc tggatctggt     120
caggataccg caattcgtgt ttttgcaatt cctccgagct ttgcaagcat ttttctgacc     180
aaaagcacca aactgacctg tctggttacc gatctgacca cctatgatag cgttaccatt     240
agctggaccc gtcagaatgg tgaagcagtt aaaacccata ccagcattag cgaaagccat     300
ccgagcgcaa cctttagcgc agttggtgaa gcaagcattt ctgaagatga ttggaatagc     360
ggtgaacgtt ttacctgtac cgttacccat accgatctgc cgtcaccgct gaaacagacc     420
attagccgtc gaaaggtgg atcctaataa gcttggtacc                            460
```

<210> SEQ ID NO 22
<211> LENGTH: 165
<212> TYPE: PRT
<213> ORGANISM: Artificial
<220> FEATURE:
<223> OTHER INFORMATION: Sc-RP-CH4-M-P
<220> FEATURE:
<221> NAME/KEY: DOMAIN
<222> LOCATION: (37)..(165)
<223> OTHER INFORMATION: IgM-CH4 domain

<400> SEQUENCE: 22

```
Gly Ser Gly Gly Gly Ser Gly Gly Gly Ser Gly Gly Gly Gly
1               5                  10                  15
Ser Ser Gly Gly Gly Ser Gly Gly Gly Ser Gly Gly Gly
            20                  25                  30
Ser Gly Ser Gly Val Ala Leu His Arg Pro Asp Val Tyr Leu Leu Pro
        35                  40                  45
Pro Ala Arg Glu Gln Leu Asn Leu Arg Glu Ser Ala Thr Ile Thr Cys
    50                  55                  60
Leu Val Thr Gly Phe Ser Pro Ala Asp Val Phe Val Gln Trp Met Gln
65                  70                  75                  80
Arg Gly Gln Pro Leu Ser Pro Glu Lys Tyr Val Thr Ser Ala Pro Met
                85                  90                  95
Pro Glu Pro Gln Ala Pro Gly Arg Tyr Phe Ala His Ser Ile Leu Thr
            100                 105                 110
Val Ser Glu Glu Glu Trp Asn Thr Gly Glu Thr Tyr Thr Cys Val Ala
        115                 120                 125
His Glu Ala Leu Pro Asn Arg Val Thr Glu Arg Thr Val Asp Lys Ser
    130                 135                 140
Thr Gly Lys Pro Thr Leu Tyr Ser Val Ser Leu Val Met Ser Asp Thr
145                 150                 155                 160
Ala Gly Thr Ser Tyr
                165
```

<210> SEQ ID NO 23
<211> LENGTH: 529
<212> TYPE: DNA
<213> ORGANISM: Artificial
<220> FEATURE:
<223> OTHER INFORMATION: Sc-RP-CH4-M-N

<400> SEQUENCE: 23

```
gagctcggat ccggatctgg tggaggcgga tctggcggtg gaggcagcgg aggtggcgga      60
```

| | |
|---|---:|
| agctcaggtg gcggtggaag tggcggtggt ggtagtggtg gcggtggctc tggttctggt | 120 |
| gttgcactgc atcgtccgga tgtttatctg ctgcctccgg cacgtgaaca gctgaatctg | 180 |
| cgtgaaagcg caaccattac ctgtctggtt accggttttt ctccggcaga tgttttgtt | 240 |
| cagtggatgc agcgtggtca gccgctgtct ccggaaaaat atgttaccag cgcaccgatg | 300 |
| ccggaaccgc aggcaccggg tcgttatttt gcacatagca ttctgaccgt tagcgaagaa | 360 |
| gaatggaata caggcgaaac ctatacctgt gttgcacatg aagcactgcc gaatcgtgtt | 420 |
| accgaacgta ccgttgataa aagcaccggt aaaccgaccc tgtatagcgt tagcctggtt | 480 |
| atgagcgata cagcaggcac aagctatgga tcctaataag cttggtacc | 529 |

```
<210> SEQ ID NO 24
<211> LENGTH: 29
<212> TYPE: DNA
<213> ORGANISM: Artificial
<220> FEATURE:
<223> OTHER INFORMATION: primer CH05

<400> SEQUENCE: 24
```

| | |
|---|---:|
| agttgatcag gtagcggtgg tggtggttc | 29 |

```
<210> SEQ ID NO 25
<211> LENGTH: 19
<212> TYPE: DNA
<213> ORGANISM: Artificial
<220> FEATURE:
<223> OTHER INFORMATION: primer CH04

<400> SEQUENCE: 25
```

| | |
|---|---:|
| taccaagctt attaggatc | 19 |

```
<210> SEQ ID NO 26
<211> LENGTH: 1284
<212> TYPE: DNA
<213> ORGANISM: Artificial
<220> FEATURE:
<223> OTHER INFORMATION: CAD-IgG-CH3

<400> SEQUENCE: 26
```

| | |
|---|---:|
| atgagaggat cgcatcacca tcaccatcac ggatctctgg ttccgcgtgg ttctgatgtt | 60 |
| ctgatgaccc agacaccgct gtctctgccg gttagcctgg gtgatcaggc aagcattagc | 120 |
| tgtcgtagca gccagagcat tgttcatagc aatggcaata cctatctgga atggtatctg | 180 |
| cagaaaccgg gtcagagccc gaaactgctg atttataaag tgagcaatcg ctttagcggt | 240 |
| gttccggatc gttttagcgg ttcaggttct ggcaccgatt ttaccctgaa aattagccgt | 300 |
| gttgaagcag aagatctggg cgtttattat tgttttcagg gtagccatgt tccgtatacc | 360 |
| tttggtggtg gcaccaaact ggaaattaaa cgtaccggta gcggtagtgg aggtggtgga | 420 |
| agcggtggtg gcggttctgg cggtggaggt tcttctggtg gcggtggatc aggtggaggt | 480 |
| ggctcaggcg gtggcggtag cggcagcggt gaagttcagc tgcagcagag cggtccggaa | 540 |
| ctggttaaac cgggtgcaag cgttaaaatt agctgtaaag ccagcggcta cccttacc | 600 |
| gattattata tgcattgggt tcgtcagcgt ccgggtcagg gtctggaatg gattggtgaa | 660 |
| atttatccgg gtagcggtaa taccagctat aatgaaaaat tcgtggcaa agcaaccctg | 720 |
| accgcagata aaagcagcag caccgcatat atgcagctgt ctagcctgac cagcgaagat | 780 |
| agcgcagttt acttttgtgc acgtggcacc ctggattata ccatggatta ttggggacag | 840 |
| ggcaccagcg ttaccgttag cagcggatca ggtagcggtg gtggtggttc tggcggtggt | 900 |

```
ggcagcggag gtggcggtag ctcaggtggc ggaggtagtg gcggtggagg cagtggtggc    960
ggtggctctg gatctggtga accgcaggtt tataccctgc ctccgagccg tgaagaaatg   1020
accaaaaatc aggttagcct gacctgtctg gtgaaaggtt tttatccgag cgatattgca   1080
gttgaatggg aaagcaatgg tcagccggaa ataattata aaaccacacc tccggttctg    1140
gattctgatg gtagcttttt tctgtatagc aaactgaccg ttgataaaag ccgttggcag   1200
cagggtaatg ttttttagctg tagcgttatg catgaagccc tgcataatca ttatacccag  1260
aaaagcctga gcctgggatc ctaa                                          1284
```

<210> SEQ ID NO 27
<211> LENGTH: 1293
<212> TYPE: DNA
<213> ORGANISM: Artificial
<220> FEATURE:
<223> OTHER INFORMATION: CAD-IgG-CH2

<400> SEQUENCE: 27

```
atgagaggat cgcatcacca tcaccatcac ggatctctgg ttccgcgtgg ttctgatgtt     60
ctgatgaccc agacaccgct gtctctgccg gttagcctgg gtgatcaggc aagcattagc    120
tgtcgtagca gccagagcat tgttcatagc aatggcaata cctatctgga atggtatctg    180
cagaaaccgg gtcagagccc gaaactgctg atttataaag tgagcaatcg ctttagcggt    240
gttccggatc gttttagcgg ttcaggttct ggcaccgatt ttaccctgaa aattagccgt    300
gttgaagcag aagatctggg cgtttattat tgttttcagg gtagccatgt tccgtatacc    360
tttggtggtg gcaccaaact ggaaattaaa cgtaccggta cggtagtgg aggtggtgga    420 agcggtggtg gcggttctgg cggtggaggt tcttctggtg gcggtggatc aggtggaggt    480
ggctcaggcg gtggcggtag cggcagcggt gaagttcagc tgcagcagag cggtccggaa    540
ctggttaaac cgggtgcaag cgttaaaatt agctgtaaag ccagcggcta cactttacc    600 gattattata tgcattgggt tcgtcagcgt ccgggtcagg gtctggaatg gattggtgaa    660
atttatccgg gtagcggtaa taccagctat aatgaaaaat tcgtggcaa agcaaccctg    720 accgcagata aaagcagcag caccgcatat atgcagctgt ctagcctgac cagcgaagat    780
agcgcagttt acttttgtgc acgtggcacc ctgattatca ccatggatta ttggggacag    840
ggcaccagcg ttaccgttag cagcggatca ggttctggtg ggggagggtc tggcggaggt    900
ggctctggcg gaggcggttc aagcggtggc ggaggtagtg gcggtggtgg tagtggaggc    960
ggaggctctg gttcaggtgg tccggatgtt tttctgtttc cgcctaaacc gaaagatacc   1020
ctgatgatta gccgtacacc ggaagttacc tgtgttgttg ttgatgtgag ccatgaagat   1080
ccggaagtga aatttaattg gtatgtggat ggtgtggaag ttcataatgc aaaaccaaa   1140 ccgcgtgaag aacagtataa tagcacctat cgtgttgttt ctgttctgac cgttctgcat   1200
caggattggc tgaatggcaa agaatataaa tgcaaagtgt ctaataaagc actgccgctg   1260
ccggaagaaa aaccattag caaaggatcc taa                                 1293
```

<210> SEQ ID NO 28
<211> LENGTH: 30
<212> TYPE: DNA
<213> ORGANISM: Artificial
<220> FEATURE:
<223> OTHER INFORMATION: primer CH03

<400> SEQUENCE: 28
agttgatcag gttctggtgg gggagggtct                              30

<210> SEQ ID NO 29
<211> LENGTH: 2145
<212> TYPE: DNA
<213> ORGANISM: Artificial
<220> FEATURE:
<223> OTHER INFORMATION: CAD-IgM-IgA-IgG

<400> SEQUENCE: 29

| | |
|---|---|
| atgagaggat cgcatcacca tcaccatcac ggatctctgg ttccgcgtgg ttctgatgtt | 60 |
| ctgatgaccc agacaccgct gtctctgccg gttagcctgg gtgatcaggc aagcattagc | 120 |
| tgtcgtagca gccagagcat tgttcatagc aatggcaata cctatctgga atggtatctg | 180 |
| cagaaaccgg gtcagagccc gaaactgctg atttataaag tgagcaatcg ctttagcggt | 240 |
| gttccggatc gttttagcgg ttcaggttct ggcaccgatt ttaccctgaa aattagccgt | 300 |
| gttgaagcag aagatctggg cgtttattat tgttttcagg gtagccatgt tccgtatacc | 360 |
| tttggtggtg gcaccaaact ggaaattaaa cgtaccggta gcggtagtgg aggtggtgga | 420 |
| agcggtggtg gcggttctgg cggtggaggt tcttctggtg gcggtggatc aggtggaggt | 480 |
| ggctcaggcg gtggcggtag cggcagcggt gaagttcagc tgcagcagag cggtccggaa | 540 |
| ctggttaaac cgggtgcaag cgttaaaatt agctgtaaag ccagcggcta taccttacc | 600 |
| gattattata tgcattgggt tcgtcagcgt ccgggtcagg gtctggaatg gattggtgaa | 660 |
| atttatccgg gtagcggtaa taccagctat aatgaaaaat tcgtggcaa agcaaccctg | 720 |
| accgcagata aaagcagcag caccgcatat atgcagctgt ctagcctgac cagcgaagat | 780 |
| agcgcagttt acttttgtgc acgtggcacc ctggattata ccatggatta ttggggacag | 840 |
| ggcaccagcg ttaccgttag cagcggatca ggaagtggtg aggtggcag cggtggtggt | 900 |
| ggctctggtg gaggcggtag ctcaggtggc ggtggtagtg gcggtggagg tagtggtggc | 960 |
| ggaggttctg gatctggtca ggataccgca attcgtgttt ttgcaattcc tccgagcttt | 1020 |
| gcaagcattt ttctgaccaa aagcaccaaa ctgacctgtc tggttaccga tctgaccacc | 1080 |
| tatgatagcg ttaccattag ctggaccgt cagaatggtg aagcagttaa aacccatacc | 1140 |
| agcattagcg aaagccatcc gagcgcaacc tttagcgcag ttggtgaagc aagcatttct | 1200 |
| gaagatgatt ggaatagcgg tgaacgtttt acctgtaccg ttacccatac cgatctgccg | 1260 |
| tcaccgctga acagaccat tagccgtccg aaaggtggat caggtagcgg aggtggcgga | 1320 |
| agcggaggtg gaggcagtgg tggaggcggt agctcaggtg gcggtggaag tggtggaggt | 1380 |
| ggctcagggg gtggaggttc tggttctggt cgtccggaag ttcatctgct gcctccgcct | 1440 |
| agcgaagaac tggcactgaa tgaactggtt accctgacct gtctggcacg tggttttagc | 1500 |
| ccgaaagatg ttctggttcg ttggctgcag ggtagccagg aactgcctcg cgaaaaatat | 1560 |
| ctgacctggg catctcgcca ggaaccgagc cagggcacca ccacctttgc agttaccagc | 1620 |
| attctgcgtg ttcagcagag agattggaaa aaaggcgata cctttagctg tatggttggt | 1680 |
| catgaagcac tgccgctggc atttacccag aaaaccatcg atcgcggatc aggtagcggt | 1740 |
| ggtggtggtt ctggcggtgg tggcagcgga ggtggcggta gctcaggtgg cggaggtagt | 1800 |

```
ggcggtggag gcagtggtgg cggtggctct ggatctggtg aaccgcaggt ttatacccctg   1860 cctccgagcc gtgaagaaat gaccaaaaat caggttagcc tgacctgtct ggtgaaaggt   1920
ttttatccga gcgatattgc agttgaatgg gaaagcaatg gtcagccgga aaataattat   1980
aaaaccacac ctccggttct ggattctgat ggtagctttt ttctgtatag caaactgacc   2040
gttgataaaa gccgttggca gcagggtaat gtttttagct gtagcgttat gcatgaagcc   2100
ctgcataatc attatacccca gaaaagcctg agcctgggat cctaa                 2145
```

<210> SEQ ID NO 30
<211> LENGTH: 28
<212> TYPE: DNA
<213> ORGANISM: Artificial
<220> FEATURE:
<223> OTHER INFORMATION: primer CH09

<400> SEQUENCE: 30

```
agttgatcag gaagtggtgg aggtggca                                       28
```

<210> SEQ ID NO 31
<211> LENGTH: 28
<212> TYPE: DNA
<213> ORGANISM: Artificial
<220> FEATURE:
<223> OTHER INFORMATION: primer CH07

<400> SEQUENCE: 31

```
agttgatcag gtagcggagg tggcggaa                                       28
```

<210> SEQ ID NO 32
<211> LENGTH: 135
<212> TYPE: PRT
<213> ORGANISM: Artificial
<220> FEATURE:
<223> OTHER INFORMATION: Sc-RP-CH3-Knob02-P
<220> FEATURE:
<221> NAME/KEY: DOMAIN
<222> LOCATION: (37)..(135)
<223> OTHER INFORMATION: IgG-CH3-Knob02 domain

<400> SEQUENCE: 32

Gly Ser Gly Gly Gly Gly Ser Gly Gly Gly Gly Ser Gly Gly Gly Gly
1               5                   10                  15

Ser Ser Gly Gly Gly Gly Ser Gly Gly Gly Gly Ser Gly Gly Gly Gly
            20                  25                  30

Ser Gly Ser Gly Glu Pro Gln Val Tyr Thr Leu Pro Pro Ser Arg Glu
        35                  40                  45

Glu Met Thr Lys Asn Gln Val Ser Leu Tyr Cys Leu Val Lys Gly Phe
50                  55                  60

Tyr Pro Ser Asp Ile Ala Val Glu Trp Glu Ser Asn Gly Gln Pro Glu
65                  70                  75                  80

Asn Asn Tyr Lys Thr Tyr Pro Pro Val Leu Asp Ser Asp Gly Ser Phe
                85                  90                  95

Tyr Leu Tyr Ser Lys Leu Thr Val Asp Lys Ser Arg Trp Gln Gln Gly
            100                 105                 110

Asn Val Phe Ser Cys Ser Val Met His Glu Ala Leu His Asn His Tyr
        115                 120                 125

Thr Gln Lys Ser Leu Ser Leu
    130                 135

-continued

```
<210> SEQ ID NO 33
<211> LENGTH: 423
<212> TYPE: DNA
<213> ORGANISM: Artificial
<220> FEATURE:
<223> OTHER INFORMATION: Sc-RP-CH3-Knob02-N

<400> SEQUENCE: 33
ggatccggta gcggtggtgg tggtagtggt ggcggtggtt caggtggtgg tggcagcagt      60
ggtggtggcg gttctggcgg tggcggttca ggtggcggag gtagcggtag cggtgaaccg     120
caggtttata ccctgcctcc gagccgtgaa gaaatgacca aaaatcaggt tagcctgtat     180
tgcctggtga aaggttttta tccgagcgat attgcagttg aatgggaaag caatggtcag     240
ccggaaaata actataaaac ctatccgcct gtgctggata gtgatggtag ctttatctg      300 tatagcaaac tgaccgtgga taaaagccgt tggcagcagg gtaatgtttt tagctgtagc     360
gttatgcatg aagccctgca taatcactac acccagaaaa gcctgagcct gtaataaaag     420
ctt                                                                   423

<210> SEQ ID NO 34
<211> LENGTH: 1281
<212> TYPE: DNA
<213> ORGANISM: Artificial
<220> FEATURE:
<223> OTHER INFORMATION: CAD-IgG-CH3-Knob02

<400> SEQUENCE: 34
atgagaggat cgcatcacca tcaccatcac ggatctctgg ttccgcgtgg ttctgatgtt      60
ctgatgaccc agacaccgct gtctctgccg gttagcctgg gtgatcaggc aagcattagc     120
tgtcgtagca gccagagcat tgttcatagc aatggcaata cctatctgga atggtatctg     180
cagaaaccgg gtcagagccc gaaactgctg atttataaag tgagcaatcg ctttagcggt     240
gttccggatc gttttagcgg ttcaggttct ggcaccgatt ttaccctgaa aattagccgt     300
gttgaagcag aagatctggg cgtttattat tgttttcagg gtagccatgt tccgtatacc     360
tttggtggtg gcaccaaact ggaaattaaa cgtaccggta gcggtagtgg aggtggtgga     420
agcggtggtg gcggttctgg cggtggaggt tcttctggtg gcggtggatc aggtggaggt     480
ggctcaggcg gtggcggtag cggcagcggt gaagttcagc tgcagcagag cggtccggaa     540
ctggttaaac cggtgcaag cgttaaaatt agctgtaaag ccagcggcta tacctttacc     600
gattattata tgcattgggt tcgtcagcgt ccgggtcagg gtctggaatg gattggtgaa     660
atttatccgg gtagcggtaa taccagctat aatgaaaaat tcgtggcaa gcaaccctg      720 accgcagata aaagcagcag caccgcatat atgcagctgt ctagcctgac cagcgaagat     780
agcgcagttt acttttgtgc acgtggcacc ctggattata ccatggatta ttggggacag     840
ggcaccagcg ttaccgttag cagcggatcc ggtagcggtg gtggtggtag tggtggcggt     900
ggttcaggtg gtggtggcag cagtggtggt ggcggttctg gcggtggcgg ttcaggtggc     960
ggaggtagcg gtagcggtga accgcaggtt tatacccctgc ctccgagccg tgaagaaatg    1020
accaaaaatc aggttagcct gtattgcctg gtgaaaggtt tttatccgag cgatattgca    1080
gttgaatggg aaagcaatgg tcagccggaa aataactata aaacctatcc gcctgtgctg    1140
gatagtgatg gtagcttttta tctgtatagc aaactgaccg tggataaaag ccgttggcag    1200
cagggtaatg tttttagctg tagcgttatg catgaagccc tgcataatca ctacacccag    1260
aaaagcctga gcctgtaata a                                              1281
```